(12) United States Patent
Behnke, II et al.

(10) Patent No.: US 9,039,693 B2
(45) Date of Patent: *May 26, 2015

(54) HANDHELD MEDICAL DEVICES INCLUDING MICROWAVE AMPLIFIER UNIT AT DEVICE HANDLE

(75) Inventors: Robert J. Behnke, II, Erie, CO (US); Jeffrey L. Jensen, Boulder, CO (US); Scott E. M. Frushour, Boulder, CO (US); Wayne L. Moul, Loveland, CO (US)

(73) Assignee: Covidien LP, Mansfield, MA (US)

( * ) Notice: Subject to any disclaimer, the term of this patent is extended or adjusted under 35 U.S.C. 154(b) by 835 days.

This patent is subject to a terminal disclaimer.

(21) Appl. No.: 13/237,187

(22) Filed: Sep. 20, 2011

(65) Prior Publication Data

US 2013/0072922 A1 Mar. 21, 2013

(51) Int. Cl.
 *A61B 18/18* (2006.01)
 *A61B 18/00* (2006.01)
 *A61B 19/00* (2006.01)

(52) U.S. Cl.
 CPC ... *A61B 18/1815* (2013.01); *A61B 2018/00922* (2013.01); *A61B 2018/1823* (2013.01); *A61B 2019/4836* (2013.01)

(58) Field of Classification Search
 None
 See application file for complete search history.

(56) References Cited

U.S. PATENT DOCUMENTS

| | | |
|---|---|---|
| D223,367 S | 4/1972 | Kountz |
| 4,014,343 A * | 3/1977 | Esty ............................ 606/45 |
| D263,020 S | 2/1982 | Rau, III |
| D266,842 S | 11/1982 | Villers et al. |
| D278,306 S | 4/1985 | McIntosh |
| D295,893 S | 5/1988 | Sharkany et al. |
| D295,894 S | 5/1988 | Sharkany et al. |
| D354,218 S | 1/1995 | Van de Peer |
| 5,556,377 A | 9/1996 | Rosen et al. |
| 5,871,481 A | 2/1999 | Kannenberg et al. |
| 5,961,871 A | 10/1999 | Bible et al. |
| D424,693 S | 5/2000 | Pruter |
| D424,694 S | 5/2000 | Tetzlaff et al. |
| D425,201 S | 5/2000 | Tetzlaff et al. |
| D449,886 S | 10/2001 | Tetzlaff et al. |
| D457,958 S | 5/2002 | Dycus et al. |
| D457,959 S | 5/2002 | Tetzlaff et al. |

(Continued)

FOREIGN PATENT DOCUMENTS

| | | |
|---|---|---|
| CN | 1103807 | 6/1995 |
| DE | 179607 | 3/1905 |

(Continued)

OTHER PUBLICATIONS

European Search Report dated Nov. 21, 2012 for EP 12 00 6524.

(Continued)

*Primary Examiner* — Brian T Gedeon

(57) ABSTRACT

A system includes a microwave signal generator and a medical device. The medical device includes a handle assembly, a microwave-signal-amplifying module, and a probe. The microwave-signal-amplifying module includes a microwave amplifier unit. The microwave amplifier unit is adapted to amplify a high-frequency input signal to generate a high-frequency output signal. The microwave amplifier unit is disposed within the handle assembly. The probe extends distally from the distal end of the handle assembly and is operably coupled to an output of the microwave-signal-amplifying module.

13 Claims, 8 Drawing Sheets

(56) References Cited

U.S. PATENT DOCUMENTS

| | | | |
|---|---|---|---|
| 6,383,183 | B1 | 5/2002 | Sekino et al. |
| 6,511,478 | B1 | 1/2003 | Burnside et al. |
| 6,575,969 | B1 | 6/2003 | Rittman, III et al. |
| D487,039 | S | 2/2004 | Webster et al. |
| D496,997 | S | 10/2004 | Dycus et al. |
| D499,181 | S | 11/2004 | Dycus et al. |
| D525,361 | S | 7/2006 | Hushka |
| D531,311 | S | 10/2006 | Guerra et al. |
| D533,942 | S | 12/2006 | Kerr et al. |
| D535,027 | S | 1/2007 | James et al. |
| D541,418 | S | 4/2007 | Schechter et al. |
| D541,938 | S | 5/2007 | Kerr et al |
| D564,662 | S | 3/2008 | Moses et al. |
| D574,323 | S | 8/2008 | Waaler |
| D576,932 | S | 9/2008 | Strehler |
| D594,736 | S | 6/2009 | Esjunin |
| D594,737 | S | 6/2009 | Kelly et al. |
| D606,203 | S | 12/2009 | Husheer et al. |
| D613,412 | S | 4/2010 | DeCarlo |
| 7,863,984 | B1 | 1/2011 | Behnke |
| D634,010 | S | 3/2011 | DeCarlo |
| 8,353,903 | B2 * | 1/2013 | Podhajsky .................... 606/33 |
| 8,394,092 | B2 * | 3/2013 | Brannan ........................ 606/41 |
| 8,459,525 | B2 * | 6/2013 | Yates et al. ................. 227/180.1 |
| 2002/0156471 | A1 * | 10/2002 | Stern et al. .................... 606/41 |
| 2006/0155270 | A1 | 7/2006 | Hancock et al. |
| 2008/0147056 | A1 | 6/2008 | Van Der Weide et al. |
| 2008/0249523 | A1 | 10/2008 | McPherson et al. |
| 2010/0049177 | A1 * | 2/2010 | Boone et al. .................... 606/9 |
| 2010/0079215 | A1 | 4/2010 | Brannan et al. |
| 2010/0082022 | A1 | 4/2010 | Haley et al. |
| 2010/0082023 | A1 | 4/2010 | Brannan et al. |
| 2010/0082024 | A1 | 4/2010 | Brannan et al. |
| 2010/0082025 | A1 | 4/2010 | Brannan et al. |
| 2010/0082083 | A1 | 4/2010 | Brannan et al. |
| 2010/0082084 | A1 | 4/2010 | Brannan et al. |
| 2010/0087808 | A1 | 4/2010 | Paulus |
| 2010/0094271 | A1 | 4/2010 | Ward et al. |
| 2010/0179455 | A1 * | 7/2010 | Nebrigic et al. ................ 601/15 |
| 2010/0268220 | A1 | 10/2010 | Johnson et al. |
| 2010/0286681 | A1 | 11/2010 | Podhajsky |
| 2010/0286682 | A1 | 11/2010 | Podhajsky |
| 2010/0286683 | A1 | 11/2010 | Podhajsky |
| 2010/0312234 | A1 * | 12/2010 | Mahvi et al. .................... 606/33 |
| 2011/0077639 | A1 | 3/2011 | Brannan et al. |
| 2011/0115562 | A1 | 5/2011 | Gilbert |
| 2011/0276113 | A1 * | 11/2011 | Cybulski ....................... 607/101 |
| 2012/0004652 | A1 * | 1/2012 | Moua et al. .................... 606/33 |

FOREIGN PATENT DOCUMENTS

| | | |
|---|---|---|
| DE | 390937 | 3/1924 |
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 390937 | 4/1989 |
| DE | 3904558 | 8/1990 |
| DE | 3942998 | 7/1991 |
| DE | 4238263 | 5/1993 |
| DE | 4206433 | 9/1993 |
| DE | 4303882 | 8/1994 |
| DE | 4339049 | 5/1995 |
| DE | 19506363 | 8/1996 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| EP | 0 246 350 | 11/1987 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 0 521 264 | 1/1993 |
| EP | 0 556 705 | 8/1993 |
| EP | 556705 | 8/1993 |
| EP | 0 558 429 | 9/1993 |
| EP | 608609 | 8/1994 |
| EP | 0 836 868 | 4/1998 |
| EP | 836868 | 4/1998 |
| EP | 0 882 955 | 12/1998 |
| EP | 882955 | 12/1998 |
| EP | 1051948 | 11/2000 |
| EP | 1 159 926 | 5/2001 |
| EP | 0 648 515 | 4/2003 |
| EP | 1366724 | 1/2006 |
| EP | 880220 | 6/2006 |
| EP | 1776929 | 4/2007 |
| EP | 2 345 454 A1 | 7/2011 |
| FR | 179 607 | 11/1906 |
| FR | 1 275 415 | 10/1961 |
| FR | 1275415 | 10/1961 |
| FR | 1 347 865 | 11/1963 |
| FR | 1347865 | 11/1963 |
| FR | 2 235 669 | 1/1975 |
| FR | 2 276 027 | 1/1976 |
| FR | 2 313 708 | 12/1976 |
| FR | 2313708 | 12/1976 |
| FR | 2364461 | 7/1978 |
| FR | 2 502 935 | 10/1982 |
| FR | 2502935 | 10/1982 |
| FR | 2 517 953 | 6/1983 |
| FR | 2517953 | 6/1983 |
| FR | 2 573 301 | 5/1986 |
| FR | 2573301 | 5/1986 |
| FR | 2 862 813 | 5/2005 |
| FR | 2 864 439 | 7/2005 |
| JP | 5-5106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |
| JP | 2001008944 | 1/2001 |
| JP | 2001029356 | 2/2001 |
| JP | 2001128990 | 5/2001 |

(56) References Cited

FOREIGN PATENT DOCUMENTS

| JP | 2001231870 | 8/2001 |
|---|---|---|
| JP | 2008142467 | 6/2008 |
| SU | 166452 | 11/1964 |
| SU | 166452 | 1/1965 |
| SU | 401367 | 11/1974 |
| SU | 727201 | 4/1980 |
| WO | WO02/11634 | 2/2002 |
| WO | WO02/45589 | 6/2002 |
| WO | WO03/090635 | 11/2003 |
| WO | WO2006/050888 | 5/2006 |
| WO | WO2008/053532 | 5/2008 |
| WO | WO2010/035831 | 4/2010 |
| WO | WO 2010/129348 A1 | 11/2010 |

OTHER PUBLICATIONS

European Search Report dated Jan. 7, 2013 for EP 12 18 5192.
U.S. Appl. No. 08/136,098, filed Oct. 14, 1993, Roger A. Stern.
U.S. Appl. No. 08/483,742, filed Jun. 7, 1995, Roger A. Stern.
U.S. Appl. No. 12/619,323, filed Nov. 16, 2009, Arnold V. DeCarlo.
U.S. Appl. No. 12/619,462, filed Nov. 16, 2009, Casey M. Ladtkow.
U.S. Appl. No. 12/620,289, filed Nov. 17, 2009, Joseph D. Brannan.
U.S. Appl. No. 12/642,623, filed Dec. 18, 2009, Prakash Manley.
U.S. Appl. No. 12/686,726, filed Jan. 13, 2010, Joseph D. Brannan.
U.S. Appl. No. 12/692,856, filed Jan. 25, 2010, Joseph D. Brannan.
U.S. Appl. No. 12/696,671, filed Jan. 29, 2010, Steven Kim.
U.S. Appl. No. 12/696,966, filed Jan. 29, 2010, Steven Kim.
U.S. Appl. No. 12/701,030, filed Feb. 5, 2010, Francesca Rossetto.
U.S. Appl. No. 12/708,974, filed Feb. 19, 2010, Joseph D. Brannan.
U.S. Appl. No. 12/709,014, filed Feb. 19, 2010, Joseph D. Brannan.
U.S. Appl. No. 12/712,864, filed Feb. 25, 2010, Joseph D. Brannan.
U.S. Appl. No. 12/713,429, filed Feb. 26, 2010, Anthony C. Lee.
U.S. Appl. No. 12/713,515, filed Feb. 26, 2010, Anthony C. Lee.
U.S. Appl. No. 12/713,641, filed Feb. 26, 2010, Anthony C. Lee.
U.S. Appl. No. 12/719,657, filed Mar. 8, 2010, Mani N. Prakash.
U.S. Appl. No. 12/722,034, filed Mar. 11, 2010, Casey M. Ladtkow.
U.S. Appl. No. 12/731,367, filed Mar. 25, 2010, Joseph D. Brannan.
U.S. Appl. No. 12/732,508, filed Mar. 26, 2010, Steven Kim.
U.S. Appl. No. 12/732,521, filed Mar. 26, 2010, Steven Kim.
U.S. Appl. No. 12/772,675, filed May 3, 2010, Brian Shiu.
U.S. Appl. No. 12/777,984, filed May 11, 2010, Joseph D. Brannan.
U.S. Appl. No. 12/786,671, filed May 25, 2010, Richard A. Willyard.
U.S. Appl. No. 12/787,639, filed May 26, 2010, Mani N. Prakash.
U.S. Appl. No. 12/792,904, filed Jun. 3, 2010, Ronald J. Podhajsky.
U.S. Appl. No. 12/792,932, filed Jun. 3, 2010, Ronald J. Podhajsky.
U.S. Appl. No. 12/792,947, filed Jun. 3, 2010, Ronald J. Podhajsky.
U.S. Appl. No. 12/792,970, filed Jun. 3, 2010, Ronald J. Podhajsky.
U.S. Appl. No. 12/793,037, filed Jun. 3, 2010, Ronald J. Podhajsky.
U.S. Appl. No. 12/823,211, filed Jun. 25, 2010, Mani N. Prakash.
U.S. Appl. No. 12/826,897, filed Jun. 30, 2010, Brian Shiu.
U.S. Appl. No. 12/826,902, filed Jun. 30, 2010, Brian Shiu.
U.S. Appl. No. 12/837,820, filed Jul. 16, 2010, Joseph D. Brannan.
U.S. Appl. No. 12/839,023, filed Jul. 19, 2010, Ronald J. Podhajsky.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/098,199, filed Apr. 29, 2011, Roop L. Mahajan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991 ), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With The LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure™"Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-108 Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds in Urology 1999, vol. 1, Issue 4, pp. 10-17.

(56) References Cited

OTHER PUBLICATIONS

Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasce. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol., BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

LigaSure™ Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants". Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157
"Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.

(56) References Cited

OTHER PUBLICATIONS

Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.—Medical Professionals: Targis™Technology (Date Unknown). "Overcoming the Challenge" located at: <http://www.urologix.com!medicaUtechnology.html > last visited on Apr. 27, 2001, 3 pages.
Urrutia et al., (1988). "Retractable-Barb Needle for Breast Lesion Localization: Use in 60 Cases," Radiology 169(3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSure™ Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Seatch Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001019 dated Sep. 23, 2008.

(56) References Cited

OTHER PUBLICATIONS

European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10158944.8 extended dated Jun. 21, 2010.
European Search Report EP 10161722.3 extended dated Jun. 16, 2010.
European Search Report EP 10163235.4 dated Aug. 10, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/USO4/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/793,136, filed Jun. 3, 2010, Gary M. Couture.
U.S. Appl. No. 12/823,703, filed Jun. 25, 2010, Mark A. Johnston.
U.S. Appl. No. 12/826,879, filed Jun. 30, 2010, Christopher A. Deborski.
U.S. Appl. No. 12/834,364, filed Jul. 12, 2010, David S. Keppel.
U.S. Appl. No. 12/845,203, filed Jul. 28, 2010, Gary M. Couture.
U.S. Appl. No. 12/985,063, filed Jan. 5, 2011, Robert J. Behnke, II.
U.S. Appl. No. 13/034,822, filed Feb. 25, 2011, Mark A. Johnston.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/227,704, filed Sep. 8, 2011, Thomas Plaven.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/246,035, filed Sep. 27, 2011, Darren Odom.
U.S. Appl. No. 13/247,043, filed Sep. 28, 2011, Donald W. Heckel.
Vallfors et al., "Automatically Controlled Bipolar Electrosoagulation-'COA-COMP'" Neurosurgical Review 7:2-3 (1984) pp. 187-190.
Prutchi et al. "Design and Development of Medical Electronic Instrumentation", John Wiley & Sons, Inc. 2005.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.

(56) References Cited

OTHER PUBLICATIONS

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11155959.7 dated Jun. 30, 2011.
International Search Report EP11155960.5 dated Jun. 10, 2011.
International Search Report PCT/US03/33711 dated Jul. 16, 2004.
International Search Report PCT/US03/33832 dated Jun. 17, 2004.
International Search Report PCT/USO4/02961 dated Aug. 2, 2005.
International Search Report PCT/US04/13443 dated Dec. 10, 2004.
International Search Report PCT/US09/46870 dated Jul. 21, 2009.

\* cited by examiner

HANDHELD MEDICAL DEVICES INCLUDING MICROWAVE AMPLIFIER UNIT AT DEVICE HANDLE

BACKGROUND

1. Technical Field

The present disclosure relates to handheld medical devices suitable for use in tissue ablation applications. More particularly, the present disclosure relates to medical devices with a microwave amplifier unit at the device handle, electrosurgical systems including the same, methods of directing energy to tissue using the same, and methods of manufacturing the same.

2. Discussion of Related Art

Electrosurgical instruments have become widely used by surgeons. Electrosurgery involves the application of thermal and/or electrical energy to cut, dissect, ablate, coagulate, cauterize, seal or otherwise treat biological tissue during a surgical procedure. Electrosurgery is typically performed using a handpiece including a surgical instrument (e.g., end effector or ablation probe) adapted to transmit energy to a tissue site during electrosurgical procedures, a remote electrosurgical generator operable to output energy, and a cable assembly operatively connecting the surgical instrument to the remote generator.

In various open and laparoscopic surgeries, it is necessary to coagulate, seal or weld tissues. A number of devices are available that can be used to provide high bursts of energy for short periods of time to coagulate, cauterize, cut and/or seal tissue. By utilizing an electrosurgical forceps, a surgeon can cauterize, coagulate, desiccate and/or cut tissue and/or simply reduce or slow bleeding by controlling the intensity, frequency and duration of the electrosurgical energy applied through the end effector to the tissue. The energy is generated by a remote generator and applied to the tissue via electrodes that are electrically connected via a cable assembly to the generator.

Treatment of certain diseases requires the destruction of malignant tissue growths, e.g., tumors. In the treatment of diseases such as cancer, certain types of tumor cells have been found to denature at elevated temperatures that are slightly lower than temperatures normally injurious to healthy cells. Known treatment methods, such as hyperthermia therapy, heat diseased cells to temperatures above 41° C. while maintaining adjacent healthy cells below the temperature at which irreversible cell destruction occurs. These methods may involve applying electromagnetic radiation to heat, ablate and/or coagulate tissue. There are a number of different types of electrosurgical apparatus that can be used to perform ablation procedures.

Typically, microwave apparatus for use in ablation procedures include a microwave generator that functions as an energy source and a microwave surgical instrument (e.g., microwave ablation probe) having an antenna assembly for directing the energy to the target tissue. The surgical instrument and microwave generator are typically operatively coupled by a cable assembly having a plurality of conductors for transmitting energy from the remote generator to the surgical instrument, and for communicating control, feedback and identification signals between the instrument and the remote generator. There are several types of microwave probes in use, e.g., monopole, dipole and helical, which may be used in tissue ablation applications.

A variety of types of handheld instruments utilizing electromagnetic radiation have been employed for various types of electrosurgery in a variety of types of applications. Cable assemblies are typically employed to mechanically connect the handheld instruments to remote energy sources and to serve as a propagation medium and waveguide for the radiofrequency (RF) or microwave signal. Parameters used to evaluate the electrical performance of microwave cable assemblies include attenuation of the cable (also known as insertion loss, i.e., loss of power due to inserting the cable between the source and the load), voltage standing-wave ratio (VSWR) characteristics, and the shielding of the cable's outer conductor. Stray leakage of microwave energy from the cable assembly may cause interference to deployed wireless networks, patient monitoring, and other medical equipment used in a hospital environment. Cable assemblies add cost to produce and maintain the microwave surgical instruments. Cable assemblies may also interfere with the surgeon's full freedom of movement during use of a handheld instrument to perform procedures utilizing electromagnetic radiation to treat tissue.

SUMMARY

According to an aspect, a medical device is provided. The medical device includes a handle assembly. A probe extends distally from a distal end of the handle assembly. A microwave amplifier unit is disposed within the handle assembly. The microwave amplifier unit is adapted to amplify a high-frequency input signal to generate a high-frequency output signal to be transmitted to the probe.

The medical device may include a microwave-signal-amplifying module. The microwave amplifier unit may include one or more outputs electrically-coupled to one or more outputs of the microwave-signal-amplifying module. The microwave amplifier unit may be disposed within the microwave-signal-amplifying module. In addition or alternatively, the medical device may include a controller electrically-coupled to the microwave-signal-amplifying module and/or electrically-coupled to the microwave amplifier unit. The controller may be adapted to control one or more operating parameters (e.g., temperature, impedance, power, current, voltage, mode of operation, and/or duration of application of electromagnetic energy) associated with the microwave-signal-amplifying module.

According to another aspect, a medical device is provided that includes a handle assembly including a handle body defining a chamber therein. The medical device includes a microwave-signal-amplifier/controller module disposed within the chamber. The microwave-signal-amplifier/controller module includes a microwave amplifier unit and a controller. The microwave amplifier unit is adapted to amplify a high-frequency input signal to generate a high-frequency output signal. The controller is adapted to control one or more operating parameters (e.g., temperature, impedance, power, current, voltage, mode of operation, and/or duration of application of electromagnetic energy) associated with the microwave-signal-amplifier/controller module. The medical device includes a probe extending distally from the distal end of the handle assembly. The probe is operably coupled to an output of the microwave-signal-amplifier/controller module.

The microwave amplifier unit may include one or more outputs electrically-coupled to one or more outputs of the microwave-signal-amplifier/controller module. The controller may be adapted to control one or more operating parameters (e.g., temperature, impedance, power, current, voltage, mode of operation, and/or duration of application of electromagnetic energy) associated with the microwave amplifier unit.

In any of the aspects, the medical device may include one or more electrical conductors associated with the handle assembly (and/or handle body) for providing one or more electrically-conductive pathways. In any of the aspects, the handle assembly (and/or handle body) may be adapted to allow the microwave-signal-amplifying module or the microwave-signal-amplifier/controller module to be removable from the handle assembly. The microwave-signal-amplifying module or the microwave-signal-amplifier/controller module may include one or more connector portions provided with one or more electrical connectors or terminals suitable for making electrical connections with electrical conductors associated with the handle assembly (and/or handle body). The one or more connector portions may be configured to be removably coupleable to electrical conductors associated with the handle assembly (and/or handle body).

In any of the aspects, the microwave-signal-amplifying module or the microwave-signal-amplifier/controller module may additionally include a signal generator adapted to generate high-frequency signals (e.g., microwave signals) to be transmitted to an input of the microwave amplifier unit. One or more outputs of the signal generator may be electrically-coupled to one or more inputs of the microwave amplifier unit.

According to another aspect, a medical device is provided. The medical device includes a probe and a handle assembly. The handle assembly includes a handle body defining a first chamber therein and configured to support the probe at a distal end thereof. A microwave-signal-amplifying module including a microwave amplifier unit is disposed within the first chamber. The probe is operably coupled to an output of the microwave-signal-amplifying module. The handle assembly further includes a grip member defining a second chamber therein. The grip member is coupled to the handle body. A power-supply/controller module is disposed within the second chamber. The power-supply/controller module includes a controller adapted to control one or more operating parameters associated with the microwave-signal-amplifying module. The grip member is adapted to allow the power-supply/controller module to be removable from the handle assembly.

In any of the aspects, the medical device may be adapted to allow a user to select a signal source for high-frequency signals to be received at an input of the microwave amplifier unit. The medical device may additionally, or alternatively, include a switch adapted to enable the user to selectively switch between the signal generator and an external source of high-frequency signals.

According to yet another aspect, a medical device is provided. The medical device includes a handle assembly and a probe-and-amplifier assembly. The handle assembly includes a handle body defining a chamber therein. The probe-and-amplifier assembly includes a probe extending distally from a distal end of the handle assembly. The probe-and-amplifier assembly further includes a microwave amplifier unit disposed within the chamber. The microwave amplifier unit is coupled to a proximal end of the probe and adapted to amplify a high-frequency input signal to generate a high-frequency output signal to be transmitted to the probe. The handle body is adapted to releaseably engage the probe-and-amplifier assembly to allow removal of the probe-and-amplifier assembly from the handle assembly.

The probe may be releaseably mechanically coupled to the microwave amplifier unit to allow the probe to be separated from the amplifier, e.g., to facilitate cleaning and/or serialization of the probe and/or to permit replacement of the microwave amplifier unit.

In any of the aspects, the medical device may include a user interface, e.g., configured to provide user-input capabilities and/or capabilities for simplified use and/or programming of the medical device. The user interface may be adapted to enable a user to selectively configure one or more operating parameters of the medical device, or component thereof, e.g., depending upon a particular purpose and/or to achieve a desired surgical outcome. The user interface may include a screen, such as a flat-panel display, e.g., an LCD (liquid crystal display), plasma display panel (PDP), organic light emitting diode (OLED), or electro-luminescent display (ELD). The screen may be located at the handle assembly. The screen may be communicatively-coupled to the controller. The medical device may additionally, or alternatively, include one or more user-input devices, e.g., pointing device (joystick, trackball, etc.) and/or touchscreen. The user-input device(s) may be ergonomically located at the handle assembly. The user-input device(s) may be communicatively-coupled to the controller. The user interface may additionally, or alternatively, include an indicator unit adapted to provide perceptible sensory alerts. The indicator unit may be communicatively-coupled to the controller.

According to yet another aspect, a system is provided. The system includes a microwave signal generator and a medical device. The medical device includes a handle assembly including a handle body defining a chamber therein. The medical device further includes a probe-and-amplifier assembly. The probe-and-amplifier assembly includes a probe extending distally from a distal end of the handle assembly and a microwave amplifier unit disposed within the chamber. The microwave amplifier unit and the probe are mechanically coupled to one another to form a unitary body.

According to yet another aspect, a system is provided. The system includes a microwave signal generator and a medical device. The medical device includes a handle assembly. The medical device further includes a microwave-signal-amplifying module disposed within the handle assembly and a probe extending distally from a distal end of the handle assembly. The probe is operably coupled to the microwave-signal-amplifying module. The microwave-signal-amplifying module is adapted to amplify a high-frequency input signal to generate a high-frequency output signal.

In any of the aspects, the medical device may include a self-contained power source. The self-contained power source may be disposed within a grip-member chamber defined in a grip member of the handle assembly of the medical device. The self-contained power source may be disposed within a handle-body chamber defined in a handle body of the handle assembly of the medical device. The grip member and/or the handle body of the handle assembly of the medical device may be adapted to allow the self-contained power source to be removable from the handle assembly.

According to yet another aspect, a method of directing energy to tissue is provided. The method includes the initial step of providing a handheld device including an energy applicator and a handle assembly configured to support the energy applicator at a distal end thereof. The method also includes the step of transmitting energy from an output of a microwave amplifier unit disposed within the handle assembly through the energy applicator to tissue.

According to still another aspect, a method of directing energy to tissue is provided. The method includes the initial step of providing a handheld device including a microwave-signal-amplifying module at a handle assembly of the device and a probe including an antenna assembly operably coupled to the microwave-signal-amplifying module. The microwave-signal-amplifying module includes a microwave amplifier unit adapted to amplify a high-frequency input signal to generate a high-frequency output signal. The method also includes the step of transmitting energy from an output of the microwave amplifier unit through the antenna assembly to tissue.

According to still another aspect, a method of manufacturing a medical device is provided. The method includes the initial steps of providing a handle assembly and providing a microwave-signal-amplifying module (or microwave-signal-amplifier/controller module). The handle assembly includes a handle body defining a chamber therein. The handle body is configured to support an energy applicator at a distal end thereof. The microwave-signal-amplifying module includes a microwave amplifier unit adapted to amplify a high-frequency input signal to generate a high-frequency output signal. The microwave-signal-amplifying module includes one or more connector portions including one or more electrical connectors adapted to be removably coupleable to one or more electrical conductors associated with the handle body. The method also includes the step of positioning the microwave-signal-amplifying module into the chamber, or portion thereof, to bring the one or more electrical connectors of the one or more connector portions into electrical engagement with one or more electrical connectors associated with the handle body.

According to still another aspect, a method of manufacturing a medical device is provided. The method includes the initial step of providing a handle assembly including a handle body defining a chamber therein, an energy applicator extending distally from a distal end of the handle body, and one or more electrical conductors associated with the handle body for providing one or more electrically-conductive pathways. One of the one or more electrical conductors provides an electrically-conductive pathway from the chamber, or portion thereof, to the energy applicator. The method also includes the step of providing a microwave-signal-amplifying module (or microwave-signal-amplifier/controller module) including a microwave amplifier unit adapted to amplify a high-frequency input signal to generate a high-frequency output signal. The microwave-signal-amplifying module may additionally include a signal generator adapted to generate the high-frequency input signal to be transmitted to an input of the microwave amplifier unit. The method also includes the step of positioning the microwave-signal-amplifying module into the chamber, or portion thereof, to bring one or more electrical conductors of one or more connector portions of the microwave-signal-amplifying module into electrical engagement with the one or more electrical conductors associated with the handle body.

In any of the aspects, the microwave amplifier unit may include a solid-state amplifier having one or more high-frequency switching elements. The one or more high-frequency switching elements may include one or more Gallium Nitride Metal-Oxide Semiconductor Field-Effect Transistors (GaN MOSFETs).

BRIEF DESCRIPTION OF THE DRAWINGS

Objects and features of the presently-disclosed handheld medical device with a microwave amplifier unit at the device handle, electrosurgical systems including the same, methods of directing energy to tissue using the same, and methods of manufacturing the same will become apparent to those of ordinary skill in the art when descriptions of various embodiments thereof are read with reference to the accompanying drawings, of which.

DETAILED DESCRIPTION

Figure 1:
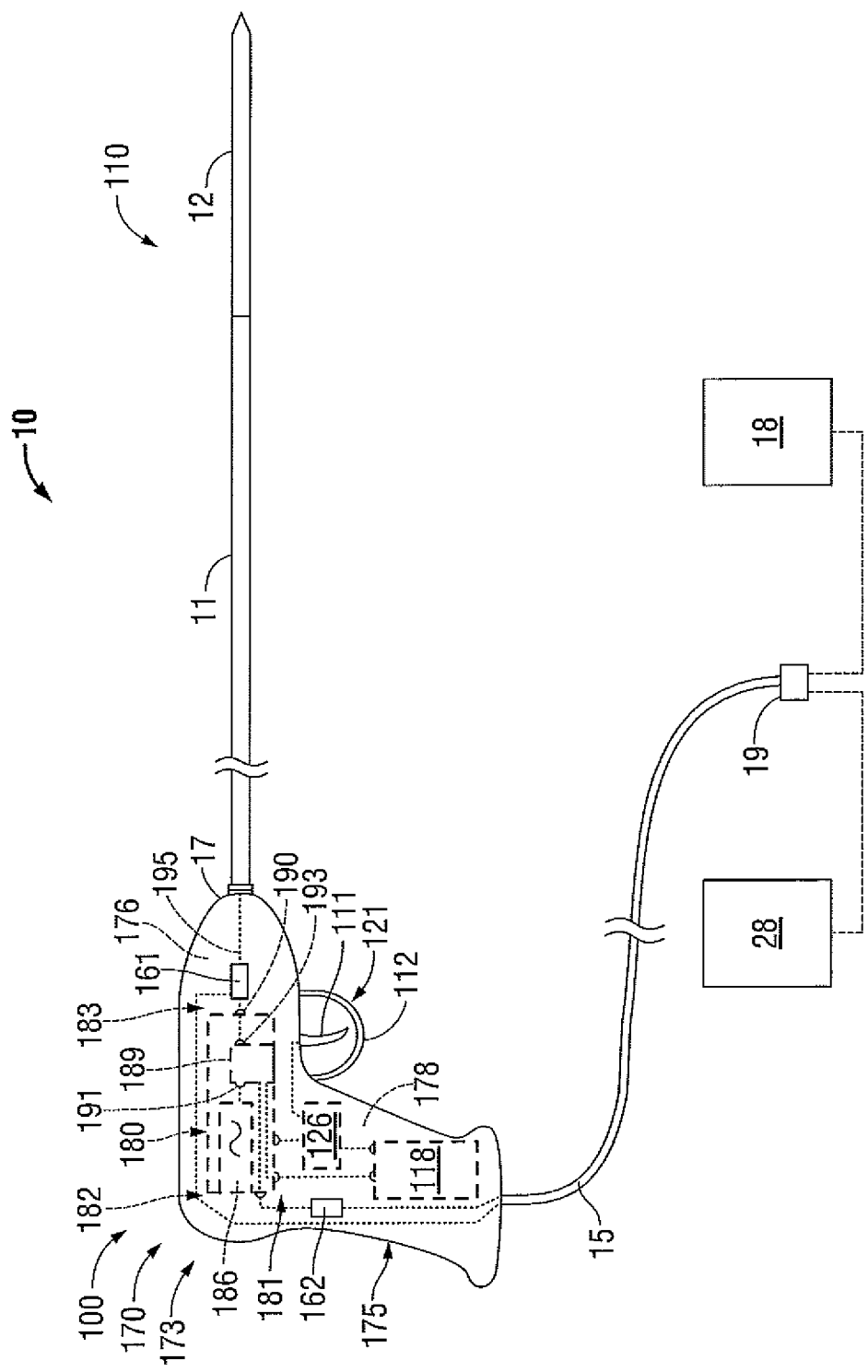
FIG. 1 is a schematic diagram of an electrosurgical system that includes a medical device in accordance with an embodiment of the present disclosure.

Hereinafter, embodiments of the presently-disclosed handheld medical device with a microwave amplifier unit at the device handle, electrosurgical systems including the same, methods of directing energy to tissue using the same, and methods of manufacturing the same will be described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user. In the following description, well-known functions or constructions are not described in detail to avoid obscuring the present disclosure in unnecessary detail.

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation or microwave ablation-assisted resection. As it is used in this description, "energy applicator" generally refers to any device that can be used to transfer energy from a power generating source, such as a microwave or RF electrosurgical generator, to tissue.

As used herein, the terms "power source" and "power supply" refer to any source (e.g., battery) of electrical power in a form that is suitable for operating electronic circuits. As it is used in this description, "transmission line" generally refers to any transmission medium that can be used for the propagation of signals from one point to another. As it is used in this description, "switch" or "switches" generally refers to any electrical actuators, mechanical actuators, electro-mechanical actuators (rotatable actuators, pivotable actuators, toggle-like actuators, buttons, etc.), optical actuators, or any suitable device that generally fulfills the purpose of connecting and disconnecting electronic devices, or component thereof, instruments, equipment, transmission line or connections and appurtenances thereto, or software.

As it is used in this description, "amplifier" generally refers to a device that produces an electrical output that is a function of the corresponding electrical input parameter, and increases the magnitude of the input by means of energy drawn from an external source (e.g., it introduces gain), or in some situations it is possible that the amplifier may have a gain of zero or unity gain. In general, a gain (amplification) is expressed as a positive decibel value, a loss (attenuation) is expressed as a negative decibel value, and unity gain (no gain) is expressed as zero decibels. In a power amplifier, the gain is usually defined as the ratio of the power output to the power input of the amplifier.

As it is used in this description, "electronic device" generally refers to a device or object that utilizes the properties of electrons or ions moving in a vacuum, gas, or semiconductor. As it is used herein, "electronic circuitry" generally refers to the path of electron or ion movement, as well as the direction provided by the device or object to the electrons or ions. As it is used herein, "electrical circuit" or simply "circuit" generally refers to a combination of a number of electrical devices and conductors that when connected together, form a conducting path to fulfill a desired function, such as amplification. Any constituent part of an electrical circuit other than the interconnections may be referred to as a "circuit element."

As it is used in this description, "user interface" generally refers to any visual, graphical, tactile, audible, sensory or other mechanism for providing information to and/or receiving information from a user or other entity. The term "user interface" as used herein may refer to an interface between a human user (or operator) and one or more devices to enable communication between the user and the device(s). Examples of user interfaces that may be employed in various embodiments of the present disclosure include without limitation, switches, potentiometers, buttons, dials, sliders, a mouse, keyboard, keypad, joysticks, trackballs, display screens, various types of graphical user interfaces (GUIs), touch screens, microphones and other types of sensors or devices that may receive some form of human-generated stimulus and generate a signal in response thereto. As it is used herein, "computer" generally refers to anything that transforms information in a purposeful way. For the purposes of this description, the term "code" should be interpreted as being applicable to software, firmware, or a combination of software and firmware.

Various embodiments of the present disclosure provide a handheld medical device with a microwave-signal-amplifying module at the handle assembly of the device operably coupled to a suitable energy applicator or probe for employing electromagnetic energy at microwave frequencies to produce a therapeutic effect on targeted tissue at a surgical site. Embodiments may be implemented using electromagnetic radiation at microwave frequencies or at other frequencies.

Various embodiments of the presently-disclosed medical device with a microwave-signal-amplifying module at the device handle are capable of directing energy into tissue, and may be suitable for use in a variety of procedures, e.g., microwave cutting, sealing, and coagulation. Various embodiments of the presently-disclosed medical device with a microwave-signal-amplifying module at the device handle and electrosurgical system including the same are suitable for microwave ablation and for use to pre-coagulate tissue for microwave ablation-assisted surgical resection. In addition, although the following description describes the use of a medical device with an energy applicator adapted for percutaneous energy delivery, the devices disclosed herein may be used with, or incorporated into, any suitable type of electrosurgical energy delivery device, such as, for example, an open device, a catheter-type device, an endoscopic device, and a direct-contact, surface-delivery device.

Various embodiments of the presently-disclosed handheld medical device entirely eliminate the need for remote electrosurgical power supplies and controllers. In some embodiments, the handheld medical device has no power or control cords, e.g., it is self-powered and all control circuitry and power supplies reside in the handle assembly of the device. Embodiments provide various configurations for locating control circuitry and microwave circuitry, some of which allow the circuitry to be entirely removed from the handheld device and modularly exchanged with other circuitry, e.g., to meet the needs of the surgical team for hospital, surgery center, and/or office-based procedures.

Various embodiments of the presently-disclosed handheld medical device include a handle assembly including a handle body defining therein a first chamber (also referred to herein as a "handle-body chamber") and a grip member defining therein a second chamber (also referred to herein as a "grip-member chamber"). Although the following description describes the use of a handle assembly including a handle body configured to support an energy applicator or probe at a distal end thereof and a grip member coupled to the handle body and adapted to be gripped by the user, the teachings of the present disclosure may also apply to a handle assembly including a handle body configured to support an energy applicator or probe at a distal end thereof and adapted to be gripped by the user.

Figure 3:
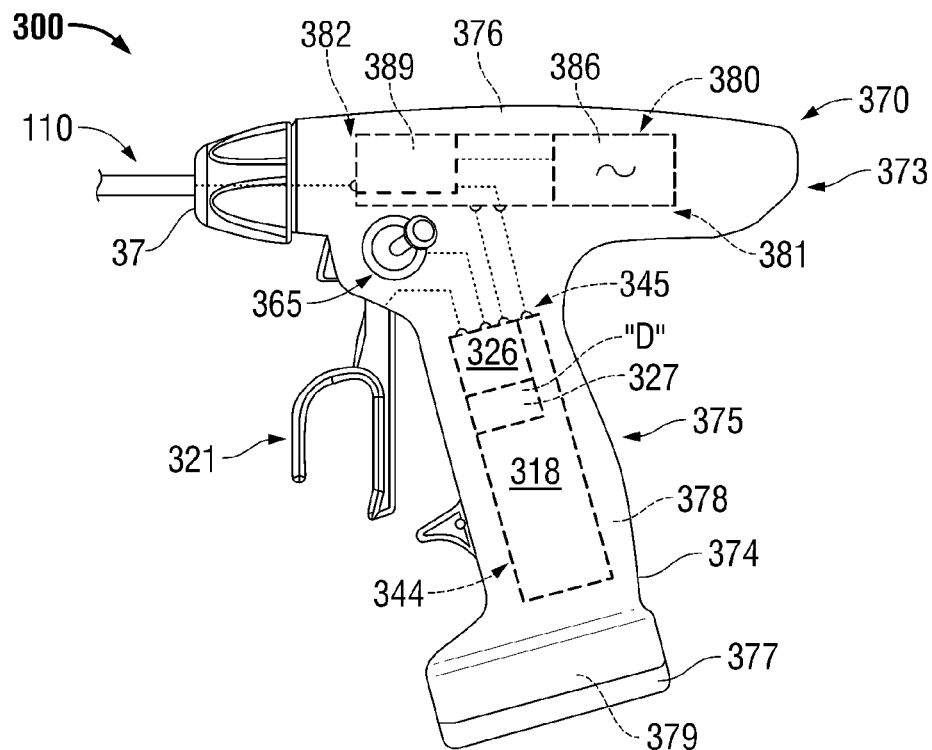
FIG. 3 is a schematic diagram of a medical device including a microwave-signal-amplifying module in the device handle in accordance with an embodiment of the present disclosure.
Figure 4:
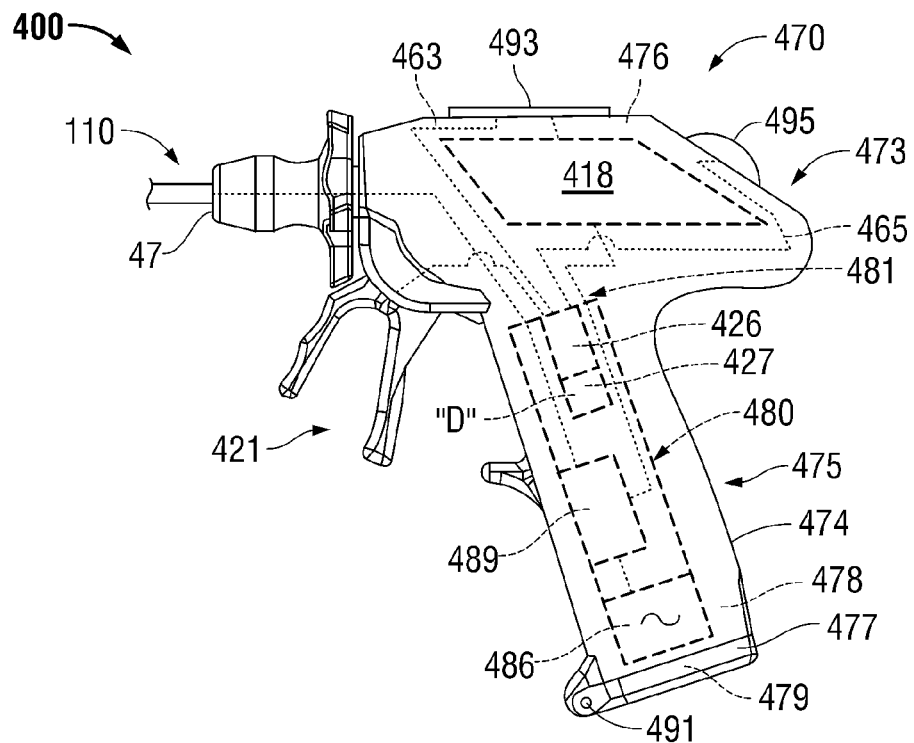
FIG. 4 is a schematic diagram of a medical device including a microwave-signal-amplifier/controller module in the device handle in accordance with the present disclosure.
Figure 6:
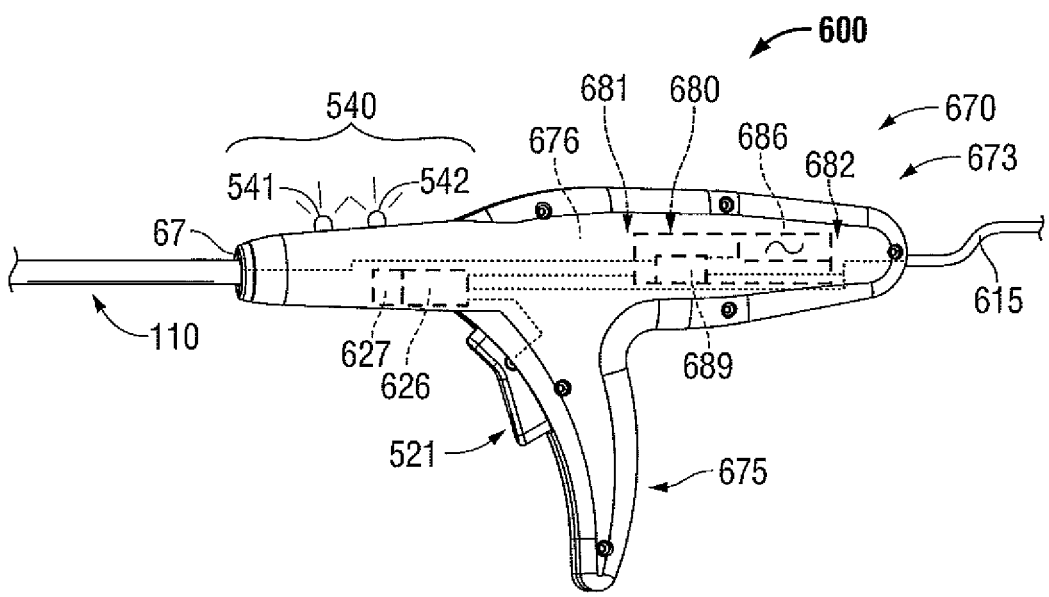
FIG. 6 is a schematic diagram of a medical device with an electrosurgical generator in the device handle in accordance with the present disclosure.

In some embodiments, as shown in FIGS. 1, 3 and 6, a microwave-signal-amplifying module 180, 380 and 680 is disposed within a handle-body chamber 176, 376 and 676, respectively, defined in a handle body 173, 373 and 673, respectively, of a handle assembly 170, 370 and 670, respectively, of a handheld medical device 100, 300 and 600, respectively. In some embodiments, as shown in FIG. 3, a power-supply/controller module 344 is disposed within a grip-member chamber 378 defined in a grip member 375 of a handle assembly 370 of a handheld medical device 300. In some embodiments, as shown in FIG. 4, a microwave-signal-amplifier/controller module 480 is disposed within a grip-member chamber 478 of a handle assembly 470 of a handheld medical device 400.

Various embodiments of the presently-disclosed handheld medical device are adapted to allow the surgeon to select an energy applicator, probe, or end-effector assembly suitable for a particular application, as desired. In some embodiments, as shown in FIG. 5, a handheld medical device 500 is provided with a microwave amplifier unit 589 incorporated with a probe 100 as a unitary body (referred to herein as a probe-and-amplifier assembly 510), wherein the probe-and-amplifier assembly 510 is releaseably coupleable with the handle assembly 570 of the medical device 500.

Figure 5:
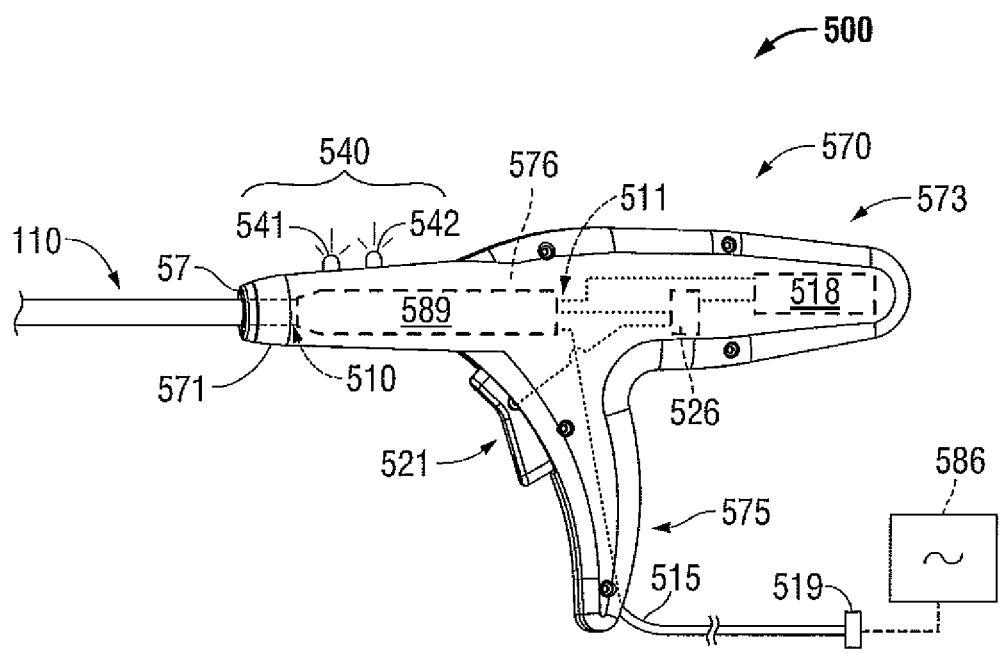
FIG. 5 is a schematic diagram of still another embodiment of a medical device including a probe-and-amplifier assembly in the device handle in accordance with the present disclosure.

In some embodiments, a transmission line 515 (e.g., shown in FIG. 5) is provided to connect a microwave amplifier unit 589 (e.g., shown in FIG. 5) disposed within the handle-body chamber 576 (e.g., shown in FIG. 5) to a remote signal generator 586 (e.g., shown in FIG. 5). In other embodiments, a transmission line 15 (e.g., shown in FIG. 1) is provided to connect the probe 110 to a remote electrosurgical power generating source.

FIG. 1 shows an electrosurgical system 10 according to an embodiment of the present disclosure that includes a handheld medical device 100 including a microwave-signal-amplifying module 180 in the handle assembly 170 of the medical device 100. Handle assembly 170 may have various configurations, some of which allow the microwave-signal-amplifying module 180 to be entirely removed from the medical device 100 and modularly exchanged with other microwave-signal-amplifying modules. Microwave-signal-amplifying module 180 includes a microwave amplifier unit 189. Microwave amplifier unit 189 generally includes one or more inputs (e.g., input 191) and one or more outputs (e.g., output 193). In some embodiments, as shown in FIG. 1, the microwave-signal-amplifying module 180 includes a signal generator 186 capable of generating high-frequency signals, e.g., microwave signals, to be transmitted to an input 191 of the microwave amplifier unit 189.

Handle assembly 170 generally includes a grip member 175 and a handle body 173 configured to support an energy applicator or probe 110 at a distal end 17 thereof. Probe 110 may be electrically-coupled to the output 190 of the microwave-signal-amplifying module 180 and/or the output 193 of the microwave amplifier unit 189 by an electrical conductor of any suitable configuration, e.g., a transmission line 195 adapted to transmit the high-frequency signals outputted from the microwave amplifier unit 189 to the probe 110. Probe 100 may include one or more antennas of any suitable type, such as an antenna assembly (or antenna array) suitable for use in tissue ablation applications. For ease of explanation and understanding, the probe 100 is described as including a single antenna assembly 12.

Handle assembly 170 may be adapted to provide various configurations of electrical connections between the power on/off switch 121, the self-contained power source 118, and/or the microwave-signal-amplifying module 180, or component thereof, e.g., microwave amplifier unit 189. It is to be understood that the dotted lines indicative of electrical connections (e.g., electrical conductors) between various components of the medical device 100 shown in FIG. 1 are merely illustrative and non-limiting examples of electrical connections, and that medical device embodiments of the present disclosure may utilize many different configurations of electrical connections, some with fewer, or additional, electrical connections than depicted in FIG. 1.

Microwave-signal-amplifying module 180 may include one or more connector portions provided with one or more electrical connectors or terminals suitable for making electrical connections with certain of the circuitry of the handle assembly 170. In some embodiments, as shown in FIG. 1, the microwave-signal-amplifying module 180 includes a first connector portion 181 having a plurality of electrical connectors or terminals for making electrical connections with the circuitry of the handle assembly 170, a second connector portion 182 having one electrical connector or terminal for making an electrical connection with the probe 110, and a third connector portion 183 having one electrical connector (or terminal) for use as an output, e.g., for making an electrical connection with the probe 110 and/or circuitry (e.g., switch 161) associated therewith. The shape and size of the handle assembly 170 and the microwave-signal-amplifying module 180 may be varied from the configuration depicted in FIG. 1.

Microwave amplifier unit 189 may include one or more power amplifiers and/or other suitable mechanism adapted to amplify a high-frequency input signal to generate a high-frequency output signal to be transmitted to the probe 110. Microwave amplifier unit 189 may include means to process and/or filter the signal. Microwave amplifier unit 189 may be solid state, and may provide high output power and/or high efficiency over a broad frequency range. Microwave amplifier unit 189 generally includes an active element suitable for amplifying a microwave signal, and may use switching to achieve high power efficiency. In simple terms, a switching amplifier consists of a periodically driven switch (active element) connected to a passive load network, which may be assumed to be linear and time-invariant. Microwave amplifier unit 189 may be implemented using active elements of various kinds, and its implementation may depend on factors determined by the device providing the input signal and/or the energy applicator or probe 110 to which the output signal is sent. Microwave amplifier unit 189 may include one or more solid-state amplifiers with high-frequency switching elements, e.g., to allow for high-efficiency amplifier topologies to be utilized, such as the class-E or its variants, class-F, or inverse class-F designs. Examples of suitable high-frequency switching elements include without limitation, Gallium Nitride Metal-Oxide Semiconductor Field-Effect Transistors (GaN MOSFETs).

In some embodiments, as shown in FIG. 1, the microwave-signal-amplifying module 180 includes a signal generator 186 electrically-coupled to an input 191 of the microwave amplifier unit 189. Signal generator 186 may include any suitable type of device capable of generating high-frequency, e.g., microwave, signals to be transmitted to the microwave amplifier unit 189. Medical device 100 may additionally, or alternatively, be adapted to selectively enable the microwave amplifier unit 189 to receive signals from a remote signal generator, e.g., a standalone signal generator 586 (e.g., shown in FIG. 5), or a remote electrosurgical power generating source 28 or component thereof, e.g., signal generator 206.

Medical device 100 may additionally, or alternatively, be adapted to selectively enable the probe 110 to receive one or more electrical signals and/or electrosurgical energy from a remote electrosurgical power generating source 28. In some embodiments, the handle assembly 170 may include a switch 161 adapted to enable the user to control operations of the medical device 100 by selectively switching between the microwave-signal-amplifying module 180, or component thereof (e.g., output 190 shown in FIG. 1), and a remote electrosurgical power generating source 28, or component thereof (e.g., generator connector 209 shown in FIG. 2).

In some embodiments, as shown in FIG. 1, the handle assembly 170 includes a self-contained power source 118, a controller 126, and a power on/off trigger or switch 121. Power on/off switch 121 may be electrically-coupled to the controller 126. In some embodiments, the controller 126 is communicatively-coupled to one or more detectors, e.g., radiation detector (not shown), and configured to override operation of the power on/off switch 121 in response to an electrical signal generated by the one or more detectors.

Controller 126 may include any type of computing device, computational circuit, or any type of processor or processing circuit capable of executing a series of instructions that are stored in a memory (e.g., 626 shown in FIG. 6) associated with the controller 126, where memory may be any device or medium that can store code and data, e.g., data associated with the probe 110, data associated with the microwave-signal-amplifying module 180 or component thereof, and/or other data. Functions of the controller 126 can be performed in hardware and/or software, as desired. Controller 126 may include logic, circuitry and/or code adapted to control the self-contained power source 118 responsive to one or more electrical signals received from the power on/off switch 121. Controller 126 may be adapted to run an operating system platform and application programs. Controller 126 may receive user-inputs from one or more user-input devices, including without limitation, a joystick, trackball, touch-screen, and/or other user-input device, e.g., the power on/off switch 121 and/or an intensity controller (not shown), communicatively-coupled to the controller 126.

In some embodiments, as shown in FIG. 1, the controller is electrically-coupled to the microwave-signal-amplifying module 180, and may be adapted to control one or more operating parameters associated with the microwave-signal-amplifying module 180, or component thereof, e.g., microwave amplifier unit 189. Examples of operating parameters associated with the electrosurgical power generating source include without limitation temperature, impedance, power, current, voltage, mode of operation, and duration of application of electromagnetic energy.

Figure 2:
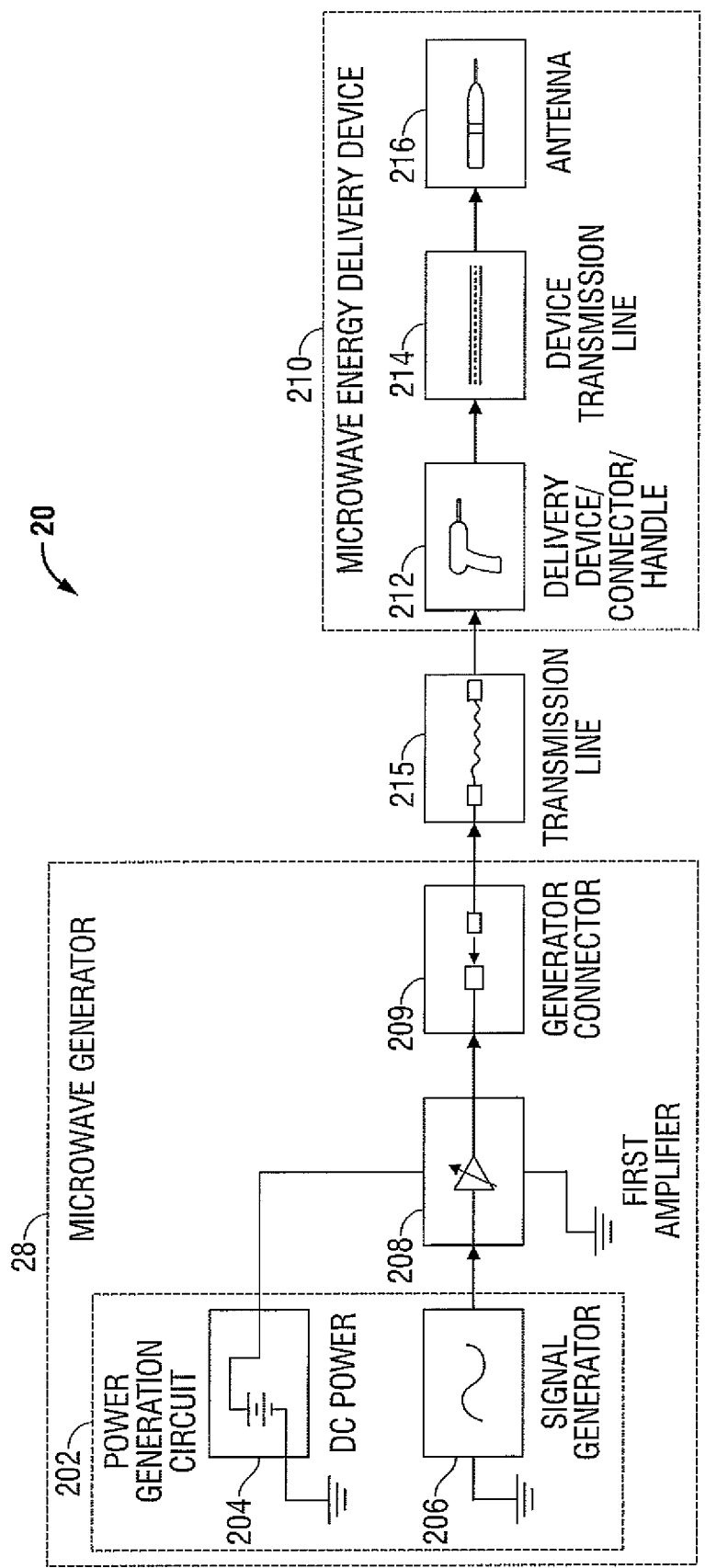
FIG. 2 is a block diagram illustrating the various functional components of a conventional microwave generation and delivery system.

In some embodiments, the handle assembly 170 may include a switch 162 adapted to enable the user to selectively switch between the signal generator 186 and a remote signal generator (e.g., signal generator 206 shown in FIG. 2). Switch 161 may be communicatively-coupled to the controller 126, and the controller 126 may be adapted to allow the user to selectively enable the microwave amplifier unit 189 to receive signals from a remote signal generator, e.g., a standalone signal generator 586 (e.g., shown in FIG. 5), or a remote electrosurgical power generating source 28 or component thereof, e.g., signal generator 206.

Handle assembly 170 may be formed of any suitable material or combination of materials by any suitable process. In some embodiments, the grip member 175 may be integrally associated with the handle body 173. Handle assembly 170 or portions thereof, e.g., grip member 175 and/or handle body 173, may be formed from two housing halves (not shown). Each half of the housing may include a series of mechanical interfacing components (not shown) configured to matingly engage with a corresponding series of mechanical interfaces (not shown) to align the two housing halves about the inner components and assemblies of the medical device 100. It is contemplated that the housing halves (as well as other components described herein) may be assembled together with the aid of alignment pins, snap-like interfaces, tongue and groove interfaces, locking tabs, adhesive ports, etc., utilized either alone or in combination for assembly purposes.

In some embodiments, the handle body 173 defines therein a handle-body chamber 176 having an interior space configured to accommodate at least the microwave-signal-amplifying module 180 therein, and the grip member 175 defines therein a grip-member chamber 178 having an interior space configured to accommodate at least a self-contained power source 118 therein. Handle body 173 may include one or more internal walls (not shown) configured to partition the grip-member chamber 178 into one or more compartments, e.g., a sealable battery-holding compartment. In some configurations, the grip-member chamber 178 has sufficient interior space to contain a self-contained power source 118 and a controller 126 therein, which may be disposed in separate compartments defined by one or more internal walls (not shown) within the grip member 175.

Handle-body chamber 176 and/or the grip-member chamber 178 may include an open end communicatively associated with an opening defined in the handle body 173 and/or the grip member 175. In such case, the opening may be covered by a removable cover plate, e.g., to allow removal of the microwave-signal-amplifying module 180, the self-contained power source 118 and/or other components of the medical device 100 disposed within, or otherwise associated with, the handle-body chamber 176, or portion thereof, and/or the grip-member chamber 178, or portion thereof.

Probe 100 may include one or more antennas of any suitable type, such as an antenna assembly (or antenna array) suitable for use in tissue ablation applications. For ease of explanation and understanding, the probe 100 is described as including a single antenna assembly 12. In some embodiments, the, probe 100 may include a coolant chamber (not shown) defined about the antenna assembly 12 or portion thereof.

Probe 110 generally includes an antenna assembly 12 (e.g., a dipole, monopole, helical, or other suitable type of antenna assembly) having a radiating antenna portion connected by a feedline 11 (or shaft) to the handle assembly 170. Antenna assembly 12 may be a microwave antenna assembly having either a straight or looped radiating antenna portion, etc., which may be inserted into or placed adjacent to tissue to be treated. Antenna assembly 12 and the feedline 11 may have various dimensions, e.g., diameter and length. Feedline 11 may be cooled by fluid, e.g., saline or water, to improve power handling. Antenna assembly 12 may be provided with a coolant chamber (not shown). Feedline 11 may be formed from any suitable flexible, semi-rigid, or rigid microwave conductive cable, and may connect directly to the microwave-signal-amplifying module 180. Feedline 11 may additionally, or alternatively, be adapted to electrically connect the antenna assembly 12 via a transmission line 15 to a remote electrosurgical power generating source 28.

Self-contained power source 118 may be any combination of battery cells, a battery pack, fuel cell and/or high-energy capacitor for use to provide power to the medical device 100. For example, capacitors may be used in conjunction with a battery pack. In such case, the capacitors may discharge a burst of power to provide energy more quickly than batteries are capable of providing, as batteries are typically slow-drain devices from which current cannot be quickly drawn. It is envisioned that batteries may be connected to the capacitors to charge the capacitors. A battery pack may include at least one disposable battery. In such case, the disposable battery may be between about 9 volts and about 30 volts, and may be a lithium-ion battery. Lithium batteries may allow longer servicer life, thereby minimizing battery replacement. Handle assembly 170 may be adapted to allow the self-contained power source 118 to be easily removed from the device 100, e.g., to facilitate battery replacement.

Power on/off switch 121 may utilize any suitable switch configuration. Examples of switch configurations that may be suitable for use with the medical device 100 include, but are not limited to, pushbutton, toggle, rocker (e.g., 521 shown in FIGS. 5 and 6), tactile, snap, rotary, slide and thumbwheel. In some embodiments, the power on/off switch 121 includes a trigger 111 located within a trigger guard 112. The shape and size of the trigger 111 and the trigger guard 112 may be varied from the configuration depicted in FIG. 1.

As an alternative to, or in addition to, the switch 121, the handle assembly 170 may include voice input technology, which may include hardware and/or software incorporated in the controller 126, or a separate digital module connected to the controller 126. The voice input technology may include voice recognition, voice activation, voice rectification, and/or embedded speech. The user may be able to control the operation of the device in whole or in part through voice commands, e.g., freeing one or both of the user's hands for operating other instruments. Voice or other audible output may also be used to provide the user with feedback.

In some embodiments, as shown in FIG. 1, the handheld medical device 100 includes a transmission line 15 coupled to a connector 19, which further operably connects the probe 110 to a remote electrosurgical power generating source 28, e.g., a microwave or RF electrosurgical generator. In some embodiments, the remote power generating source 28 is configured to provide microwave energy at an operational frequency from about 300 MHz to about 10 GHz. The remote power generating source 28 may be configured to operate in a variety of modes such as ablation, monopolar and bipolar cutting, coagulation, and other modes. An embodiment of a remote electrosurgical generator, such as the electrosurgical power generating source 28 of FIG. 1, in accordance with the present disclosure, is shown in more detail in FIG. 2. It will be understood, however, that other standalone electrosurgical generator embodiments may also be used. In some embodiments, a distal portion of the transmission line 15 may be disposed within the handle assembly 170, e.g., within the grip member 175 and/or the handle body 173. Transmission line 15 may additionally, or alternatively, provide a conduit (not shown) configured to provide coolant fluid from a coolant source 18 to one or more components of the medical device 100.

In alternative embodiments not shown, the handle assembly 170 may include an intensity controller adapted to allow the user to adjust the power parameters (e.g., voltage, power and/or current intensity) delivered to the probe 100. Intensity settings may be preset and selected from a look-up table, e.g., based on a choice of electrosurgical instruments and/or attachments, desired surgical effect, surgical specialty and/or surgeon preference. The selection may be made automatically or selected manually by the user. The intensity values may be predetermined or adjusted by the user. A variety of intensity controller designs and different locations of the intensity controller on the handle assembly 170 may suitably be used. Examples of intensity controller embodiments are disclosed in commonly assigned U.S. Pat. No. 7,156,844, entitled "ELECTROSURGICAL PENCIL WITH IMPROVED CONTROLS", the disclosure of which is incorporated herein by reference in its entirety.

In alternative embodiments not shown, the handle assembly 170 may include a radiation detector. The radiation detector may include any suitable device capable of detecting electromagnetic radiation and converting it to another form of energy such as electrical signals, and may be electrically-coupled to the controller 126. Examples of radiation detector embodiments are disclosed in commonly assigned U.S. patent application Ser. No. 12/542,785 filed on Aug. 18, 2009, entitled "MICROWAVE ABLATION ANTENNA RADIATION DETECTOR", the disclosure of which is incorporated herein by reference in its entirety.

In alternative embodiments not shown, the medical device 100 may include a fluid-flow monitoring system adapted to monitor and/or regulate the pressure and/or flow rate of fluid and capable of generating a signal indicative of an abnormal fluid circulation condition. The fluid-flow monitoring system may include one or more sensors disposed in fluid communication with the probe 110 capable of sensing the pressure and/or flow rate of fluid flow in and/or out of the probe 110. In such case, the sensors may be electrically-coupled to the controller 126. Examples of fluid-flow monitoring system embodiments are disclosed in commonly assigned U.S. patent application Ser. No. 12/568,972 filed on Sep. 29, 2009, entitled "FLOW RATE MONITOR FOR FLUID COOLED MICROWAVE ABLATION PROBE", U.S. patent application Ser. No. 12/566,299 filed on Sep. 24, 2009, entitled "OPTICAL DETECTION OF INTERRUPTED FLUID FLOW TO ABLATION PROBE", and U.S. patent application Ser. No. 12/569,685 filed on Sep. 29, 2009, entitled "FLOW RATE MONITOR FOR FLUID COOLED MICROWAVE ABLATION PROBE", the disclosures of which are incorporated herein by reference in their entireties.

In alternative embodiments not shown, the handle assembly 170 may include a reflected-power monitoring system adapted to monitor power signals reflected from the probe 110. For example, energy may be reflected from ablated tissue and received by the antenna assembly 12. Energy not transferred to the antenna assembly 12 (e.g., when the antenna and feedline do not have matching impedances) may be reflected back towards the energy source. In some embodiments, the reflected-power monitoring system is electrically-coupled to the controller 126, and may include any suitable device capable of detecting power signals reflected back from probe 110. The power sensor may include a power sensor to monitor forward and reflected power, and may measure the power output of the microwave-signal-amplifying module 180 (and/or electrosurgical power generating source 28) that is utilized by the antenna assembly 12. Examples of power measurement system embodiments are disclosed in commonly assigned U.S. patent application Ser. No. 12/242,102 filed on Sep. 30, 2008, entitled "MICROWAVE ABLATION GENERATOR CONTROL SYSTEM", the disclosure of which is incorporated herein by reference in its entirety.

In accordance with embodiments of the present disclosure, operating parameters of the microwave-signal-amplifying module 180 and/or at least some of the information monitored by various sensors, e.g., radiation detector (not shown) and fluid-flow monitoring system (not shown), operably associated with the medical device 100 may be provided to a video screen or monitoring system in an operating room. Medical device 100 may be provided with a data port (not shown) and data may be transmitted to a receiver for the operating room monitoring system via the data port, which may be wired (e.g., FireWire®, USB, Serial RS232, Serial RS485, USART, Ethernet, HDMI, mini HDMI, etc.) and/or wireless (e.g., Bluetooth®, ANT3®, KNX®, Z-Wave®, X10®, Wireless USB, Wi-Fi®, IrDA®, NanoNet , TinyOS®, ZigBee®, 802.11 IEEE, and other radio, infrared, UHF, VHF communications and the like). Such features may facilitate monitoring by the user of the medical device 100 or other operating room or hospital personnel or remotely located persons.

FIG. 2 is a block diagram illustrating the various functional components of a conventional microwave energy generation and delivery system 20. Conventional system 20 includes a microwave generator 28, a transmission line 215 and a microwave energy delivery device 210. Microwave generator 28 includes a power generation circuit 202 that generates and provides DC power from a DC power supply 204 and a microwave signal from a signal generator 206. DC power from the DC power supply 204 and the microwave signal from the signal generator 206 are supplied to a first microwave amplifier unit 208 that amplifies the microwave signal to a desirable power level. First microwave amplifier unit 208 may include one or more power amplifiers to amplify the microwave signal generated by the signal generator 206 to a desired energy level.

The microwave signal outputted from the first microwave amplifier unit 208 is supplied to a first end of the transmission line 215 connected to the generator connector 209. The second end of the transmission line 215 connects to the delivery device connector 212 of the microwave energy delivery device 210. The microwave signal is passed through the device transmission line 214 to the antenna 216 at the distal end of the microwave energy delivery device 210.

FIG. 3 shows a handheld medical device 300 according to an embodiment of the present disclosure that includes a power-supply/controller module 344 and a microwave-signal-amplifying module 380 at a handle assembly 370 of the device 300. Handle assembly 370 may have various configurations, some of which allow the power-supply/controller module 344 and/or the microwave-signal-amplifying module 380 to be entirely removed from the handle assembly 370 of the device 300 and modularly exchanged with other power-supply/controller and/or microwave-signal-amplifying modules.

Power-supply/controller module 344, which is described in more detail later in this description, includes a self-contained power source 318, a controller 326, and a memory 327 communicatively-coupled to the controller 326. Microwave-signal-amplifying module 380 includes a microwave amplifier unit 389, and may include a signal generator 386 electrically-coupled to the microwave amplifier unit 389. Microwave amplifier unit 389 and the signal generator 386 are similar to the microwave amplifier unit 189 and the signal generator 186, respectively, shown in FIG. 1, and further description thereof is omitted in the interests of brevity.

Handle assembly 370 generally includes a grip member 375 adapted to be gripped by the user and a handle body 373 configured to support an energy applicator or probe 110 at a distal end 37 thereof. Handle assembly 370 may be formed of any suitable material or combination of materials having suitable material characteristics, e.g., a strength weight characteristic. In some embodiments, the handle assembly 370 or portion thereof may be formed of a combination of metal and plastic or other nonmetallic materials, or of entirely plastic or other nonmetallic materials, e.g., depending upon the requirements of a particular application, which can be economically produced.

Handle body 373 defines therein a handle-body chamber 376 configured to accommodate one or more components of the device 300, e.g., microwave-signal-amplifying module 380, therein. Grip member 375 includes a housing 374 defining a grip-member chamber 378 therein. Grip-member housing 374 includes an open bottom end 379 disposed in communication with the grip-member chamber 378, and may have any shape suitable to be hand gripped by the user, e.g., a generally tubular shape. Grip member 375 includes a bottom portion 377 configured to cover the open bottom end 379. In some embodiments, the bottom portion 377 may be adapted to be removably coupleable (e.g., threadedly coupleable) to the grip-member housing 374.

In some embodiments, the bottom portion 377 may be adapted to mechanically engage the grip-member housing 374 in a snap-fit manner, or may alternatively be adapted to be connected to the housing 374 in any other suitable manner. As used herein, "snap-fit" refers to the engagement or assembly of two members wherein at least one of the members has a protrusion and/or abutment that engages the other member to form an interlock that retains the members together when they are connected and at least one of the members has a resiliently deformable or deflectable portion such that the deflectable portion deflects to remove the interlock as the members are brought together and resiliently snaps back to reform the interlock when the members are together.

Medical device 300 includes a power on/off switch 321 associated with the handle assembly 370. In some embodiments, the handle assembly 370 is adapted to provide an electrical connection between the power on/off switch 321 and the controller 326, as indicated by the dotted line therebetween shown in FIG. 3. Power on/off switch 321 may be adapted to be operable, singly or in conjunction with the controller 326, to be capable of switching an electric connection from the microwave-signal-amplifying module 380 or component thereof, e.g., microwave amplifier unit 389, to the self-contained power source 318 between a connect and a disconnect state. Self-contained power source 318 disposed within or otherwise associated with the power-supply/controller module 344 is similar to the self-contained power source 118 shown in FIG. 1, and further description thereof is omitted in the interests of brevity.

Handle assembly 370 may be adapted to provide various configurations of electrical connections, e.g., one or more electric conductors suitably adapted for transfer of communication signals and/or electric power, between the power on/off switch 321, the power-supply/controller module 344, or component thereof (e.g., self-contained power source 318 and/or controller 326), and/or the microwave-signal-amplifying module 380, or component thereof (e.g., microwave amplifier unit 389). Power-supply/controller module 344 may include one or more connector portions provided with one or more electrical connectors or terminals suitable for making electrical connections with certain of the circuitry of the handle assembly 370. Microwave-signal-amplifying module 380 may include one or more connector portions provided with one or more electrical connectors or terminals suitable for making electrical connections with certain of the circuitry of the handle assembly 370.

In some embodiments, as shown in FIG. 3, the power-supply/controller module 344 includes a connector portion 345 having a plurality of electrical connectors or terminals for making electrical connections with certain of the circuitry of the handle assembly 370, and the microwave-signal-amplifying module 380 includes a first connector portion 381 having a plurality of electrical connectors or terminals for making electrical connections with certain of the circuitry of the handle assembly 370, and a second connector portion 382 having one electrical connector or terminal for making an electrical connection with the probe 110. The shape and size of the handle assembly 370, the microwave-signal-amplifying module 380, and the power-supply/controller module 344 may be varied from the configuration depicted in FIG. 3.

Controller 326 disposed within or associated with the power-supply/controller module 344 may include any type of computing device, computational circuit, or any type of processor or processing circuit capable of executing a series of instructions that are stored in the memory 327. Controller 326 may include logic, circuitry and/or code adapted to control the self-contained power source 318 and/or the microwave-signal-amplifying module 380 or component thereof (e.g., microwave amplifier unit 389) responsive to one or more electrical signals received from user-operable interface elements, such as the power on/off switch 321, an intensity controller (not shown), and/or other user-operable interface elements, including without limitation any suitable type of switch, touchscreen, pointing device (e.g., joystick or trackball), and the like. Controller 326 may be adapted to run an operating system platform and application programs.

Memory 327 with the power-supply/controller module 344 may include any device or medium that can store code and data, including, for example, energy applicator data (e.g., parameters associated with the probe 110), data associated with the microwave-signal-amplifying module 380 or component thereof, and/or other data. Parameters stored in the memory 327 in connection with an energy applicator, or an energy applicator array, may include, but are not limited to, energy applicator (or energy applicator array) identifier, energy applicator (or energy applicator array) dimensions, a frequency, an ablation length (e.g., in relation to a radiating section length), an ablation diameter, a temporal coefficient, a shape metric, and/or a frequency metric. In alternative embodiments not shown, memory may additionally, or alternatively, be disposed within or otherwise associated with the microwave-signal-amplifying module 380.

Controller 326 may be adapted to control one or more operating parameters associated with the microwave-signal-amplifying module 380, or component thereof, responsive to one or more electrical signals received from a reflected-power monitoring system (not shown), a fluid-flow monitoring system (not shown) and/or one or more sensors, e.g., radiation detector (not shown), operably associated with the medical device 300, independently or in conjunction with energy applicator data and/or other data (e.g., data associated with microwave amplifier unit 389 and/or signal generator 386) stored in the memory 327, e.g., to achieve a desired surgical outcome. Examples of operating parameters associated with the microwave-signal-amplifying module 380 include temperature, impedance, power, current, voltage, mode of operation, and duration of application of electromagnetic energy.

In some embodiments, as shown in FIG. 3, the medical device 300 includes a user-input device 365 associated with the handle assembly 370. User-input device 365 may be embodied as a pointing device (e.g., joystick or trackball) ergonomically located on the handle body 373 such that the user can control the pointing device 365 easily with thumb, finger, or palm. Handle assembly 370 may be adapted to provide an electrical connection between the pointing device 365 and the controller 326, as indicated by the dotted line therebetween shown in FIG. 3. As an alternative to (or in addition to) the pointing device 365, the medical device 300 may include voice input technology, including, for example, hardware and/or software incorporated in the controller 326, or a separate digital module (not shown) connected to the controller 326. The voice input technology may include voice-recognition, voice-activation, voice-rectification, and/or embedded-speech capabilities.

Electrical signals outputted from the pointing device 365 representative of indicative orientations of the pointing device 365 may be correlated to one or more parameters of electromagnetic energy delivery into tissue. In some embodiments, the medical device 300 is configured to adjust power parameters (e.g., voltage, power and/or current intensity) and/or the power verses impedance curve shape to affect the perceived output intensity, responsive to user-effected movement of the pointing device 365. For example, the greater the lateral displacement of the pointing device 365 in a particular direction, e.g., a distal direction, the greater the level of the power parameters transmitted to the probe 110. Intensity settings may be preset and selected from a look-up table, e.g., based on a configuration of the probe 110, desired surgical effect, surgical specialty and/or surgeon preference. The selection may be made automatically or selected manually by the user. The shape, size and location of the pointing device 365 may be varied from the configuration depicted in FIG. 3.

Although a joystick type of user-input device is depicted in FIG. 3, any type of user-input device 365 may be used such as a trackball, touchscreen, etc.

FIG. 4 shows a handheld medical device 400 according to an embodiment of the present disclosure that includes a microwave-signal-amplifier/controller module 480, a self-contained power source 418, and a user interface 491 at a handle assembly 470 of the device 400. Handle assembly 470 may have various configurations, some of which allow the microwave-signal-amplifier/controller module 480 and/or self-contained power source 418 to be entirely removed from the handle assembly 470 of the device 400 and modularly exchanged with other microwave-signal-amplifier/controller modules and/or self-contained power sources. Self-contained power source 418 is similar to the self-contained power source 118 shown in FIG. 1, except for size and shape, and further description thereof is omitted in the interests of brevity. Microwave-signal-amplifier/controller module 480 includes a microwave amplifier unit 489, a signal generator 486 electrically-coupled to the microwave amplifier unit 489, a controller 426 and a memory 427 communicatively-coupled to the controller 426.

Handle assembly 470 generally includes a grip member 475 adapted to be gripped by the user and a handle body 473 configured to support an energy applicator or probe 110 at a distal end 47 thereof. Handle assembly 470 may be adapted to releaseably engage the probe 110, e.g., to allow removal of the probe from the device 400 for sterilization or other purposes and/or to facilitate the replacement of the probe 110 with another energy applicator or probe, as desired. Handle body 473 defines therein a handle-body chamber 476 configured to accommodate one or more components of the device 400, such as, for example, the self-contained power source 418.

Grip member 475 includes a grip-member housing 474 and a bottom portion 477. Grip-member housing 474 defines a grip-member chamber 478 therein and includes an open bottom end 479 disposed in communication with the chamber 478. Grip-member chamber 478 is configured to accommodate one or more components of the device 400, e.g., the microwave-signal-amplifier/controller module 480. Bottom portion 477 of the grip member 475 is configured to cover the open bottom end 479, and may be pivotably mounted with respect to the grip-member housing 474. In some embodiments, as shown in FIG. 4, the bottom portion 477 has one end pivotally mounted about a pivot pin 491 coupled to the grip-member housing 474. Bottom portion 477 may alternatively be adapted to be connected to the housing 474 in any other suitable manner.

User interface 491 may include one or more user-input devices. In some embodiments, as shown in FIG. 4, the user interface 491 includes a trackball type pointing device 495 and a screen 493. Screen 493 may be adapted to visually display text and/or one or more user-interface elements, e.g., graphical ions, visual indicators, and/or visual cues (e.g., properties like position, color, and symmetry, when used to convey information). In some embodiments, a flat-panel display, e.g., an LCD (liquid crystal display), plasma display panel (PDP), organic light emitting diode (OLED), or electroluminescent display (ELD) may be used as the screen 493. The flat-panel display may have an ultra thin profile. Screen 493 may be may be disposed, entirely or in part, in a recess formed in the handle body 473.

In some embodiments, the screen 493 includes touch-screen capability (not shown), e.g., the ability to receive input from an object in physical contact with the screen 493, such as without limitation a stylus or user's fingertip. A user-interface element displayed on the screen 493 may have a corresponding active region, such that, by touching the screen within the active region associated with the user-interface element, an input associated with the user-interface element is received by the user interface 491. In some embodiments, the user interface 491 is adapted to enable one or more electrical signals indicative of user input, e.g., an input associated with a user-interface element, to be transmitted to the controller 426. Controller 426 may be adapted to control one or more operating parameters associated with the device 400, or component thereof, based on one or more electrical signals indicative of user input received from the user interface 491.

User interface 491 and the controller 426 may be communicatively-coupled and suitably configured to provide user-input capabilities and/or capabilities for simplified use and/or programming of the medical device 400. In some embodiments, the user interface 491 includes the screen 493 communicatively-coupled to the controller 426, and may include touchscreen capability, and may further include a pointing device 495 (and/or other user-input device) communicatively-coupled to the controller 426, to enable a user to selectively configure one or more operating parameters of the medical device 400, or component thereof, e.g., depending upon a particular purpose and/or to achieve a desired surgical outcome.

In some embodiments, the handle assembly 470 is adapted to provide an electrical connection 465 between the pointing device 495 and the controller 426. Handle assembly 470 may additionally, or alternatively, be adapted to provide an electrical connection 463 between the screen 493 and the controller 426, e.g., to provide enhanced user-interface capabilities during operation of the medical device 400. Handle assembly 470 may be adapted to provide various configurations of electrical connections between the power on/off switch 421, the self-contained power source 418, the user interface 491, or component thereof (e.g., screen 493 and/or pointing device 495), and/or the microwave-signal-amplifier/controller module 480, or component thereof (e.g., microwave amplifier unit 489 and/or controller 426). It is to be understood that the dotted lines indicative of electrical connections between various components of the medical device 400 shown in FIG. 4 are merely illustrative and non-limiting examples of electrical connections, and that medical device embodiments of the present disclosure may utilize many different configurations of electrical connections, some with fewer, or additional, electrical connections than depicted in FIG. 4. Medical device 400 may include any of the electrical connections of the medical device embodiments shown in FIGS. 1 and 3. The shape and size of the microwave-signal-amplifier/controller module 480, the self-contained power source 418, and the handle assembly 470 may be varied from the configuration depicted in FIG. 4.

Controller 426 may include any type of computing device, computational circuit, or any type of processor or processing circuit capable of executing a series of instructions that are stored in a memory (not shown) associated with the controller 426. Controller 426 may include logic, circuitry and/or code adapted to control the self-contained power source 418, the microwave amplifier unit 489, and/or the signal generator 486 responsive to one or more electrical signals received from the screen 493, singly or in conjunction with one or more electrical signals received from the pointing device 495 and/or other controls (not shown) including without limitation a switch (e.g., pushbutton switch, toggle switch, slide switch) and/or a continuous actuator (e.g., rotary or linear potentiometer, rotary or linear encoder), e.g., to achieve a desired surgical outcome. In some embodiments, a reflected-power monitoring system (not shown) is electrically-coupled to the controller 426, and may include any suitable device capable of detecting power signals reflected back from probe 110.

FIG. 5 shows a handheld medical device 500 according to an embodiment of the present disclosure that includes a microwave amplifier unit 589 and a self-contained power source 518 at a handle assembly 570 of the device 500. In some embodiments, as shown in FIG. 5, the microwave amplifier unit 589 and the probe 110 are mechanically coupled to one another to form a unitary body (referred to herein as a probe-and-amplifier assembly). In the embodiment shown in FIG. 5, the microwave amplifier unit 589 is electrically-coupled via a transmission line 515 to a connector 519, which further operably connects the microwave amplifier unit 589 to a remote signal generator 586. In alternative embodiments not shown, the medical device 500 may additionally include an intensity controller adapted to allow the user to adjust the power parameters (e.g., voltage, power and/or current intensity), a radiation detector, and/or a reflected-power monitoring system.

Handle assembly 570 generally includes a grip member 575 adapted to be gripped by the user and a handle body 573 configured to support an energy applicator or probe 110 at a distal end 57 thereof. Handle body 573 defines therein a handle-body chamber 576 configured to accommodate one or more components of the device 500, such as, for example, the microwave amplifier unit 589 and the self-contained power source 518.

Handle assembly 570 may be adapted to releaseably engage the probe-and-amplifier assembly 510, e.g., to allow removal of the probe-and-amplifier assembly 510 from the medical device 500 and/or to facilitate the replacement of the probe-and-amplifier assembly 510 with another probe-and-amplifier assembly, as desired. In some embodiments, the handle assembly 570 includes a removable portion 571, e.g., disposed at the distal 57 of the handle body 573. In some embodiments, the removable portion 571 is configured to allow removal of the probe-and-amplifier assembly 510 from the medical device 500. Removable portion 571 may be threadedly coupled, or otherwise releaseably connected, to the handle body 573. Handle assembly 570 may have various configurations, some of which allow the self-contained power source 518 to be entirely removed from the handle assembly 570 of the device 500 and modularly exchanged with other self-contained power supplies. Self-contained power source 518 is similar to the self-contained power source 118 shown in FIG. 1, and further description thereof is omitted in the interests of brevity.

Probe-and-amplifier assembly 510 may include one or more connector portions provided with one or more electrical connectors or terminals suitable for making electrical connections with certain of the circuitry of the handle assembly 570. In some embodiments, as shown in FIG. 5, the probe-and-amplifier assembly 510 includes a connector portion 511, e.g., disposed at the proximal end of the microwave amplifier unit 589, including a plurality of electrical connectors or terminals (not shown) suitable for making electrical connections with certain circuitry of the handle assembly 570.

In some embodiments, the microwave amplifier unit 589 and the probe 110 are releaseably mechanically coupled to one another, e.g., to allow removal of the probe 110 from the microwave amplifier unit 589 for sterilization or other purposes. Microwave amplifier unit 589 is similar to the microwave amplifier unit 189 shown in FIG. 1, and further description thereof is omitted in the interests of brevity.

Medical device 500 includes a controller 526, a switch 521 associated with the handle assembly 570, and may include an indicator unit 540 adapted to provide a perceptible sensory alert, which may be an audio, visual, or other sensory alarm. Indicator unit 540 according to various embodiments includes an alarm or output component (not shown) that includes logic or circuitry to generate a signal when power is provided to the indicator unit 540. In some embodiments, the indicator unit 540 is adapted to generate an audio signal and the output component includes an audio circuit with a speaker (not shown). In some embodiments, the indicator unit 540 is adapted to generate a visual signal and the output component includes a light source, such as a light-emitting diode (LED).

In some embodiments, as shown in FIG. 5, the indicator unit 540 includes a first LED 541 and a second LED 542 in a row configuration disposed on a top, distal portion of the handle body 573. During operation of the medical device 500, the first and second LEDs 541, 542, respectively, may provide information/feedback (e.g., visual feedback) to the user. The shape, size and location of the first and second LEDs 541, 542 may be varied from the configuration depicted in FIG. 5. In alternative embodiments not shown, a single LED may be utilized in place of the first and second LEDs 541, 542. Indicator unit 540 may additionally, or alternatively, be adapted to provide audio and/or other perceptible sensory alerts. Indicator unit 540 may include a display device (not shown), such as a flat panel display, e.g., a liquid crystal display (LCD), or other suitable display device, to provide information/feedback to the user. In some embodiments, the handle assembly 570 is adapted to provide an electrical connection (not shown) between the indicator unit 540 and the controller 526. Controller 526 may include logic, circuitry and/or code adapted to control the indicator unit 540 to provide perceptible sensory feedback to the user during configuration of the medical device 500, e.g., indicative of electrically-coupling of the probe-and-amplifier assembly 510 to certain circuitry of the handle assembly 570, and/or during operation of the device 500 for performing a medical procedure, e.g., an ablation procedure.

Switch 521 may be any suitable switch that generally fulfills the purpose of switching electrical circuits on and off or switching over from one electrical circuit to another. In some embodiments, the switch 521 is a rocker-type switch. In some embodiments, the handle assembly 570 is adapted to provide an electrical connection between the switch 521 and the controller 526. Handle assembly 570 may be adapted to provide various configurations of electrical connections between the microwave amplifier unit 589, the controller 526, the self-contained power source 518, and/or the switch 521. In some embodiments, the handle assembly 570 is adapted to provide electrical connections (shown by dotted lines in FIG. 5) of any suitable configuration to electrically-couple an output of the microwave amplifier unit 589 to the probe 110 and to electrically-couple one or more inputs of the microwave amplifier unit to the controller 526 and/or the self-contained power source 518. In some embodiments, a reflected-power monitoring system (not shown) is electrically-coupled to the controller 526, and may include any suitable device capable of detecting power signals reflected back from probe 110. Medical device 500 may include any of the electrical connections of the medical device embodiments shown in FIGS. 1, 3 and 4.

FIG. 6 shows a handheld medical device 600 according to an embodiment of the present disclosure that includes a microwave-signal-amplifying module 680 at a handle assembly 670 of the device 600. Handle assembly 670 generally includes a grip member 675 adapted to be gripped by the user and a handle body 673 configured to support an energy applicator or probe 110 at a distal end 67 thereof.

Handle body 673 defines therein a handle-body chamber 676 configured to accommodate one or more components of the device 600, such as, for example, the microwave-signal-amplifying module 680. Handle body 673 may include one or more internal walls (not shown) configured to partition the handle-body chamber 676 into one or more compartments, e.g., a microwave-generator-module compartment. Handle body 673 may be adapted to allow removal of the microwave-signal-amplifying module 680 and/or other components of the medical device 600 disposed within, or otherwise associated with, the handle-body chamber 676, or portion thereof.

Microwave-signal-amplifying module 680 may include one or more connector portions provided with one or more electrical connectors or terminals suitable for making electrical connections with certain of the circuitry of the handle assembly 670. In some embodiments, as shown in FIG. 6, the microwave-signal-amplifying module 680 includes a first connector portion 681, e.g., disposed at the distal end of the microwave-signal-amplifying module 680, including a plurality of electrical connectors or terminals (not shown) suitable for making electrical connections with certain circuitry of the handle assembly 670, and a second connector portion 682, e.g., disposed at the proximal end of the microwave-signal-amplifying module 680, including a plurality of electrical connectors or terminals (not shown) suitable for making electrical connections with certain circuitry of the handle assembly 670 and/or for making electrical connections with one or more remote apparatus, including without limitation, a standalone signal generator (e.g., 586 shown in FIG. 5) and/or a remote electrosurgical power generating source (e.g., 28 shown in FIG. 1) or component thereof, e.g., a signal generator (e.g., 206 shown in FIG. 2).

Microwave-signal-amplifying module 680 includes a microwave amplifier unit 689 and a signal generator 686. Microwave amplifier unit 689 and the signal generator 686 are similar to the microwave amplifier unit 189 and the signal generator 186, respectively, shown in FIG. 1, and further description thereof is omitted in the interests of brevity.

Medical device 600 includes a controller 626 and a memory 627 communicatively-coupled to the controller 626. In some embodiments, a reflected-power monitoring system (not shown) is electrically-coupled to the controller 626, and may include any suitable device capable of detecting power signals reflected back from probe 110. Medical device 600 may include any of the electrical connections of the medical device embodiments shown in FIGS. 1, 3, 4 and 5.

In some embodiments, the controller 626 may include logic, circuitry and/or code adapted to control the source of the input signal to the microwave amplifier unit 689, and be capable of switching the input signal to the microwave amplifier unit 689 between the signals generated by the signal generator 686 and the signals generated by a remote signal generator. In some embodiments, the medical device 600 may include the indicator unit 540 of FIG. 5, and the controller 626 may be configured to control the indicator unit 540 to provide perceptible sensory feedback to the user indicative of the source of the input signal to the microwave amplifier unit 689. Controller 626 is similar to the controller 426 of the 480 shown in FIG. 4, and further description thereof is omitted in the interests of brevity.

Hereinafter, methods of directing energy to tissue, in accordance with the present disclosure, are described with reference to FIGS. 7 and 8. It is to be understood that the steps of the methods provided herein may be performed in combination and in a different order than presented herein without departing from the scope of the disclosure.

Figure 7:
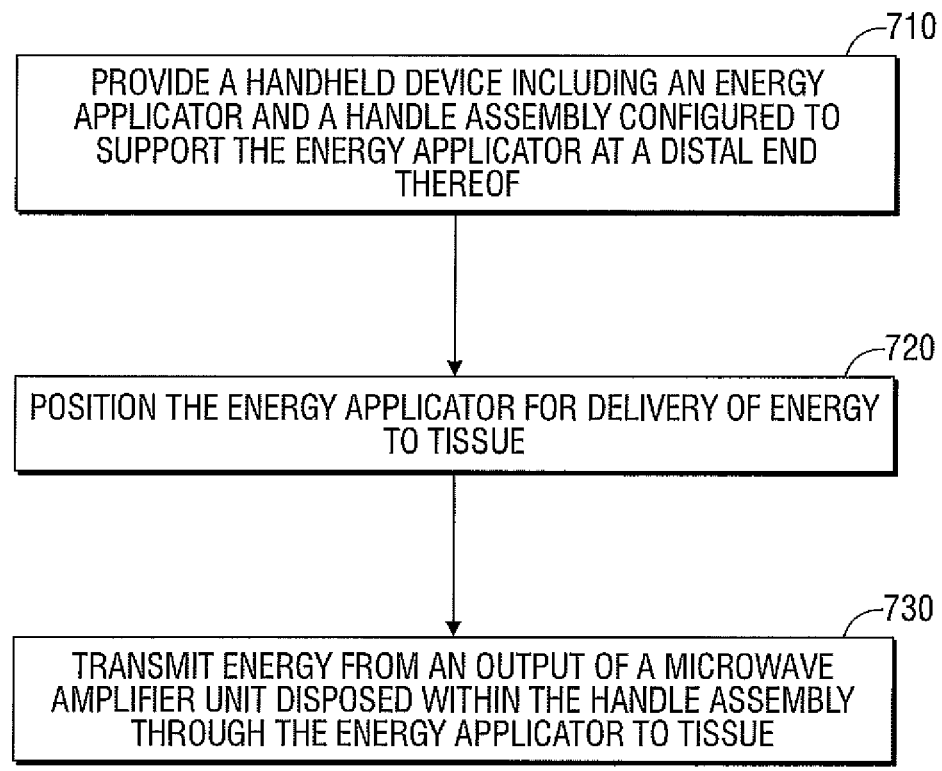
FIG. 7 is a flowchart illustrating a method of directing energy to tissue in accordance with an embodiment of the present disclosure.

FIG. 7 is a flowchart illustrating a method of directing energy to tissue according to an embodiment of the present disclosure. In step 710, a handheld device 100 is provided. Device 100 includes an energy applicator 110 and a handle assembly 170 configured to support the energy applicator 110 at a distal end 17 of the handle assembly 170.

In step 720, the probe 110 is positioned in tissue. Probe 110 may be inserted directly into tissue, inserted through a lumen, e.g., a vein, needle, endoscope or catheter, placed into the body during surgery by a clinician, or positioned in the body by other suitable methods. Ultrasound or computed tomography (CT) guidance may be used to accurately guide the probe 110 into the area of tissue to be treated. Probe 110 may be placed percutaneously or atop tissue, e.g., using conventional surgical techniques by surgical staff. Probe 110 may be configured to operate with a directional radiation pattern.

In step 730, energy is transmitted from an output 193 of a microwave amplifier unit 189 disposed within the handle assembly through the energy applicator to tissue.

Figure 8:
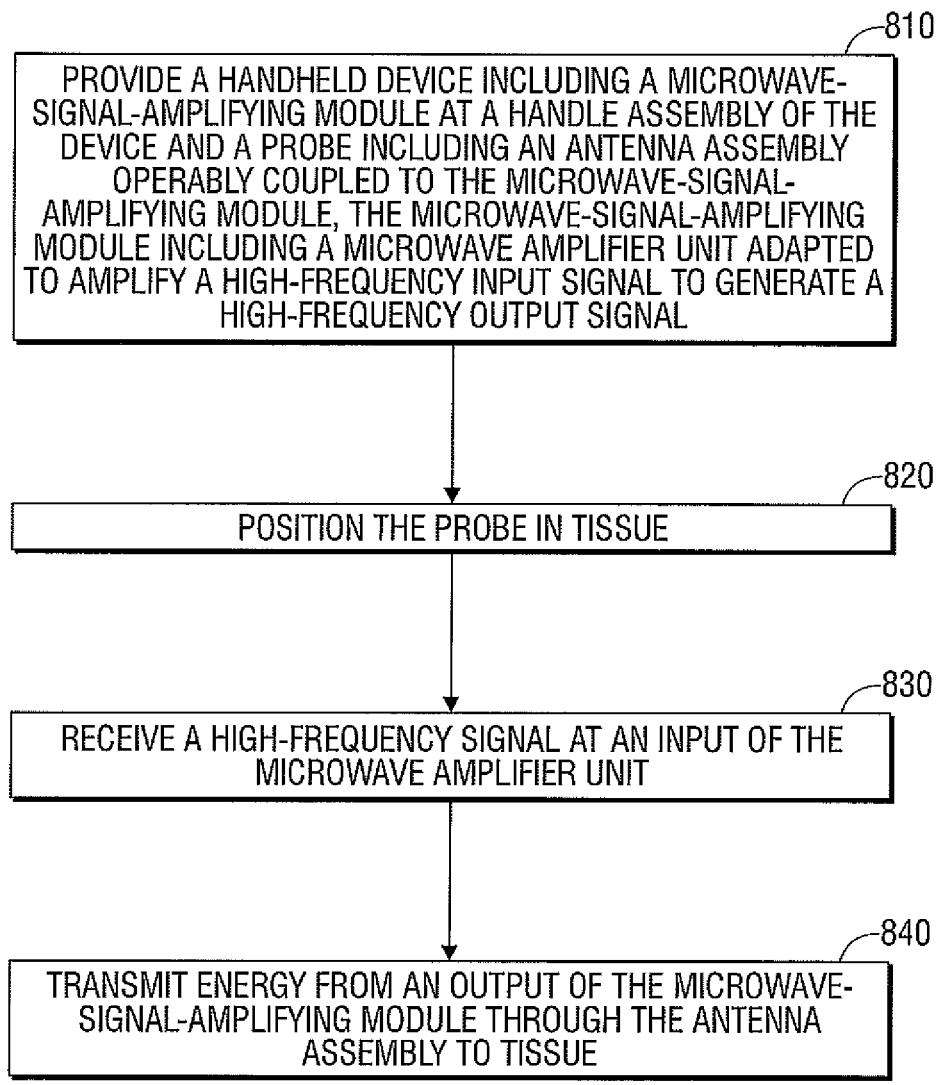
FIG. 8 is a flowchart illustrating a method of directing energy to tissue in accordance with another embodiment of the present disclosure.

FIG. 8 is a flowchart illustrating a method of directing energy to tissue according to an embodiment of the present disclosure. In step 810, a handheld device 100 is provided. Device 100 includes a microwave-signal-amplifying module 180 at a handle assembly 170 of the device 100 and a probe 110 including an antenna assembly 12 operably coupled to the microwave-signal-amplifying module 180. Microwave-signal-amplifying module 180 includes a microwave amplifier unit 189 adapted to amplify a high-frequency input signal to generate a high-frequency output signal. Microwave-signal-amplifying module 180 may further include a signal generator 186 capable of generating high-frequency, e.g., microwave, signals to be transmitted to an input of the microwave amplifier unit 189.

In step 820, the probe 110 is positioned in tissue. Probe 110 may be inserted directly into tissue, inserted through a lumen, e.g., a vein, needle, endoscope or catheter, placed into the body during surgery by a clinician, or positioned in the body by other suitable methods.

In step 830, a high-frequency signal is received at an input 191 of the microwave amplifier unit 189. In some embodiments, the handheld device 100 may be adapted to allow a user to select the signal source for high-frequency signals to be received at the input 191 of the microwave amplifier unit 189. In some embodiments, the handheld device 100 may include a switch 162 adapted to enable the user to selectively switch between a signal generator 186 disposed within the microwave-signal-amplifying module 180 and an external source 28 of high-frequency signals.

In step 840, energy is transmitted from an output of the microwave amplifier unit through the antenna assembly to tissue. A clinician may pre-determine the length of time that microwave energy is to be applied. Application duration may depend on many factors such as tumor size and location and whether the tumor was a secondary or primary cancer. The duration of microwave energy application using the probe 100 may depend on the progress of the heat distribution within the tissue area that is to be destroyed and/or the surrounding tissue.

Hereinafter, methods of manufacturing a medical device, in accordance with the present disclosure, are described with reference to FIGS. 9 and 10. It is to be understood that the steps of the methods provided herein may be performed in combination and in a different order than presented herein without departing from the scope of the disclosure.

Figure 9:
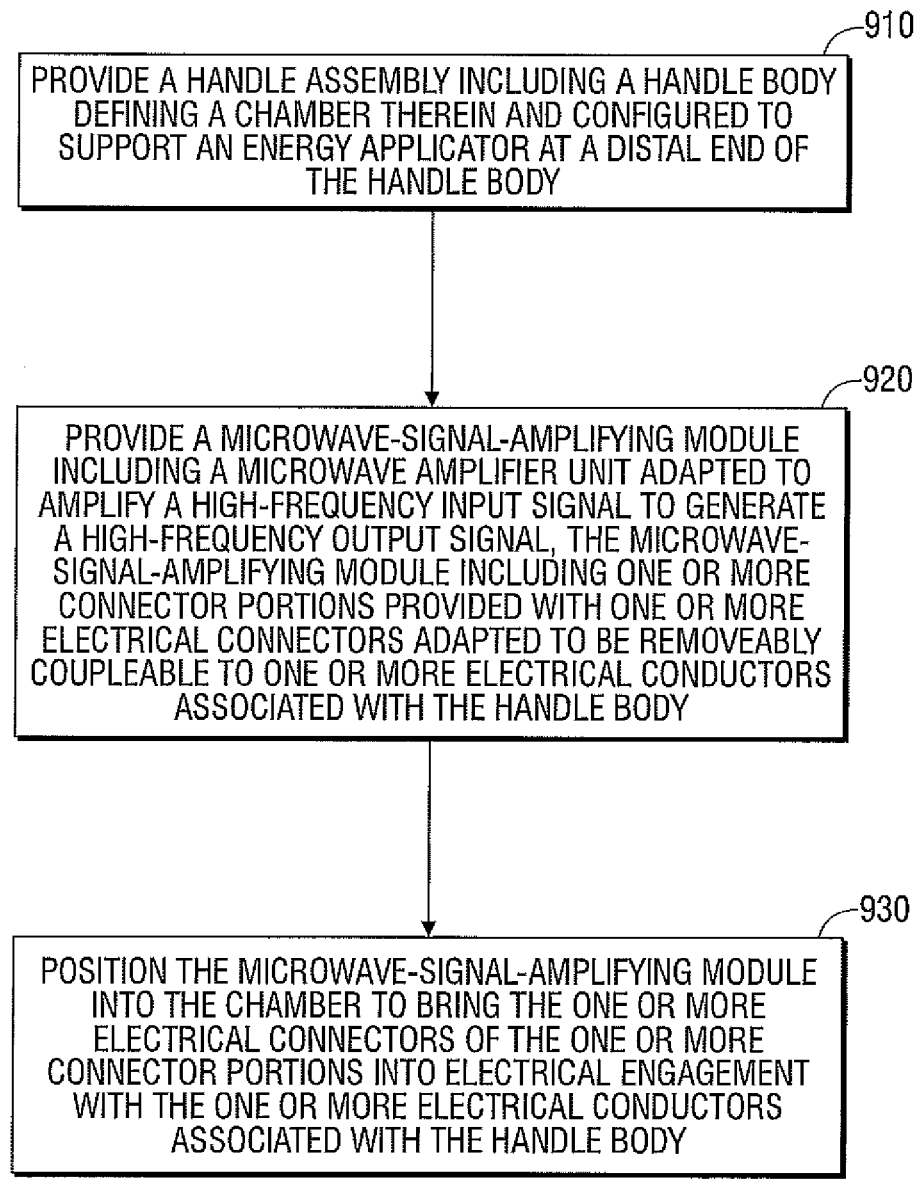
FIG. 9 is a flowchart illustrating a method of manufacturing a medical device in accordance with an embodiment of the present disclosure.

FIG. 9 is a flowchart illustrating a method of manufacturing a medical device 100 according to an embodiment of the present disclosure. In step 910, a handle assembly 170 is provided. Handle assembly 170 includes a handle body 173 defining a chamber 176 therein. Handle body 173 is configured to support an energy applicator or probe 110 at a distal end 17 thereof.

In step 920, a microwave-signal-amplifying module 180 is provided. Microwave-signal-amplifying module 180 includes a microwave amplifier unit 189 adapted to amplify a high-frequency input signal to generate a high-frequency output signal. Microwave-signal-amplifying module 180 includes one or more connector portions (e.g., three connector portions 181, 182, 183) including one or more electrical connectors (or terminals) adapted to be removeably coupleable to one or more electrical conductors associated with the handle body 173. In some embodiments, the microwave-signal-amplifying module 180 may additionally include a signal generator 186 capable of generating high-frequency, e.g., microwave, signals to be transmitted to an input 191 of the microwave amplifier unit 189.

In step 930, the microwave-signal-amplifying module 180 is positioned into the chamber 176, or portion thereof, to bring the one or more electrical connectors of the one or more connector portions into electrical engagement with the one or more electrical conductors associated with the handle body 173.

In some embodiments, the above-described method of manufacturing a medical device 100 may include the additional steps of providing an energy applicator or probe 110 and coupling the energy applicator or probe 110 at the distal end 17 of the handle body 173. Probe 100 may include one or more antennas of any suitable type, such as an antenna assembly (or antenna array) suitable for use in tissue ablation applications. Probe 110 may be electrically-coupled to the output 190 of the microwave-signal-amplifying module 180 and/or the output 193 of the microwave amplifier unit 189 by an electrical conductor of any suitable configuration, e.g., a transmission line 195 adapted to transmit the high-frequency signals outputted from the microwave amplifier unit 189 to the probe 110.

Figure 10:
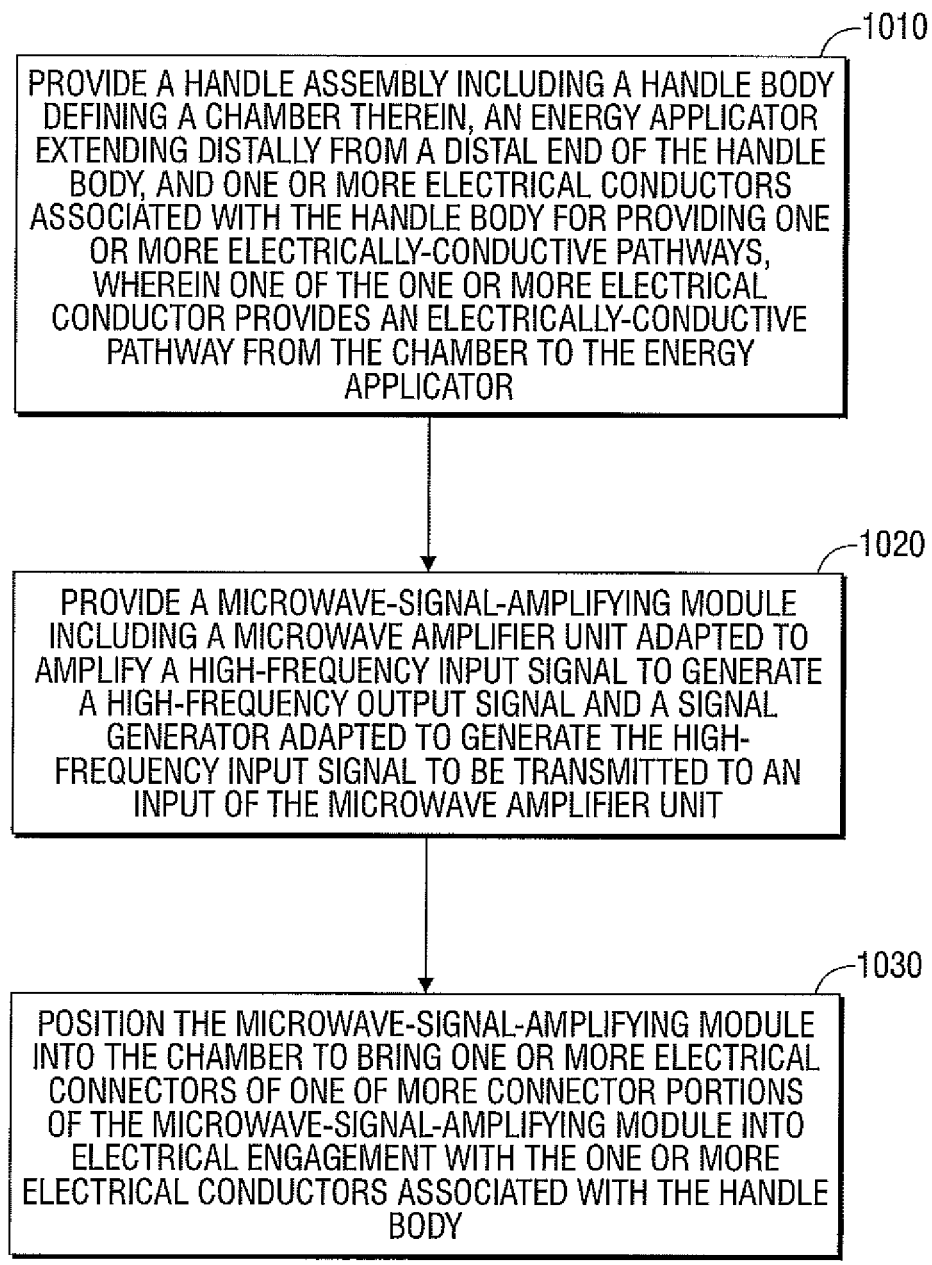
FIG. 10 is a flowchart illustrating a method of manufacturing a medical device in accordance with another embodiment of the present disclosure.

FIG. 10 is a flowchart illustrating a method of manufacturing a medical device 10 according to an embodiment of the present disclosure. In step 1010, a handle assembly 170 is provided. Handle assembly 170 includes a handle body 173 defining a chamber 176 therein. An energy applicator 110 extends distally from a distal end 17 of the handle body 173. One or more electrical conductors are associated with the handle body 173 for providing one or more electrically-conductive pathways. One of the one or more electrical conductors provides an electrically-conductive pathway 195 from the chamber 176, or portion thereof, to the energy applicator 110.

In step 1020, a microwave-signal-amplifying module 180 is provided. Microwave-signal-amplifying module 180 includes a microwave amplifier unit 189 adapted to amplify a high-frequency input signal to generate a high-frequency output signal. In some embodiments, the microwave-signal-amplifying module 180 further includes a signal generator 186 adapted to generate the high-frequency input signal to be transmitted to an input 191 of the microwave amplifier unit 189.

Microwave amplifier unit 189 may include one or more solid-state amplifiers with high-frequency switching elements, e.g., to allow for high-efficiency amplifier topologies to be utilized, such as the class-E or its variants, class-F, or inverse class-F designs. In some embodiments, the high-frequency switching elements include one or more Gallium Nitride Metal-Oxide Semiconductor Field-Effect Transistors (GaN MOSFETs).

In step 1030, the microwave-signal-amplifying module 180 is positioned into the chamber 176, or portion thereof, to bring one or more electrical conductors of one or more connector portions (e.g., three connector portions 181, 182, 183) of the microwave-signal-amplifying module 180 into electrical engagement with the one or more electrical conductors associated with the handle body 173.

A method of manufacturing another embodiment of a handheld medical device with a microwave amplifier unit at the device handle according to the present disclosure includes the initial steps of providing a handle assembly 470 and providing a microwave-signal-amplifier/controller module 480. Microwave-signal-amplifier/controller module 480 may include a microwave amplifier unit 489, a signal generator 486 electrically-coupled to the microwave amplifier unit 489, a controller 426 and a memory 427 communicatively-coupled to the controller 426. In some embodiments, the microwave-signal-amplifier/controller 480 is positioned into a chamber 478, or portion thereof, defined in a grip portion 475 of the handle assembly 470.

The above-described methods of manufacturing a medical device provide handheld medical devices with a microwave amplifier unit at the device handle suitable for use in conjunction with a variety of energy applicators, probes, or end-effector assemblies for various types of electrosurgery.

The above-described handheld medical devices with a microwave amplifier unit at the device handle, systems including the same, and methods of directing energy to tissue using the same may be used in conjunction with a variety of energy applicators or probes adapted for treating tissue. Embodiments may be used in conjunction with any suitable energy applicators or probes adapted to direct energy to tissue, such as ablation probes, e.g., placed percutaneously or surgically, and/or energy applicators suitable for use in surface ablation applications.

The above-described handheld medical devices may be used in conjunction an energy applicator or probe with a directional radiation pattern. Embodiments may be used in conjunction with a directional reflector assembly coupled to the energy applicator or probe. Some embodiments of the above-described handheld medical device are adapted to allow the surgeon to select an energy applicator or probe suitable for a particular application, as desired.

The above-described handheld medical devices with a microwave amplifier unit at the device handle and systems including the same may be suitable for a variety of uses and applications, including medical procedures, e.g., tissue ablation, resection, cautery, vascular thrombosis, treatment of cardiac arrhythmias and dysrhythmias, electrosurgery, etc. The above-described handheld medical devices with a microwave amplifier unit at the device handle and systems including the same may be suitable for use in a variety of procedures, e.g., microwave cutting, sealing, and coagulation.

Some embodiments of the above-described handheld medical devices with a microwave amplifier unit at the device handle and systems including the same entirely eliminate the need for remote electrosurgical power supplies and controllers. In some embodiments, the above-described handheld medical devices with a microwave amplifier unit at the device handle are self-powered and all control circuitry and power supplies reside in the handle assembly of the device. In some configurations, the above-described handheld medical devices have no power or control cords.

In the above-described handheld medical devices with a microwave amplifier unit at the device handle, the handle assembly of the device may have various configurations, some of which allow a microwave-signal-amplifier module (or microwave-signal-amplifier/controller module) and/or a self-contained power source to be entirely removed from the handle assembly of the device and modularly exchanged with other microwave-signal-amplifier modules (or microwave-signal-amplifier/controller modules) and/or self-contained power sources.

The above-described handheld medical devices with a microwave amplifier unit at the device handle and systems including the same may include a user interface adapted to enable a user to selectively configure one or more operating parameters of the device, or component thereof, e.g., depending upon a particular purpose and/or to achieve a desired surgical outcome.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A system, comprising:
   a microwave signal generator; and
   a medical device, including:
   a handle assembly including a first plurality of electrical contacts disposed thereon;
   a microwave-signal-amplifying module including:
   a microwave amplifier unit disposed within the handle assembly adapted to amplify a high-frequency input signal to generate a high-frequency output signal; and
   a second plurality of electrical contacts coupled to the microwave amplifier being selectively engageable with the first plurality of electrical contacts of the handle assembly; and
   a probe extending distally from a distal end of the handle assembly and operably coupled to an output of the microwave-signal-amplifying module;
   wherein the microwave-signal-amplifying module is selectively removable from the handle assembly.

2. The system of claim 1, wherein an output of the microwave amplifier unit is electrically-coupled to the output of the microwave-signal-amplifying module.

3. The system of claim 2, wherein the microwave amplifier unit includes a solid-state amplifier having at least one high-frequency switching element.

4. The system of claim 3, wherein the at least one high-frequency switching element includes at least one Gallium Nitride Metal-Oxide Semiconductor Field-Effect Transistor (GaN MOSFET).

5. The system of claim 1, wherein the microwave-signal-amplifying module further includes a signal generator capable of generating high-frequency signals to be transmitted to an input of the microwave amplifier unit.

6. The system of claim 5, wherein the handle assembly is adapted to allow the user to select a signal source for high-frequency signals to be received at an input of the microwave amplifier unit.

7. The system of claim 6, further comprising a switch adapted to enable a user to selectively switch between the signal generator and an external source of high-frequency signals.

8. The system of claim 1, further comprising a controller electrically-coupled to the microwave-signal-amplifying module and adapted to control at least one operating parameter associated with the microwave-signal-amplifying module.

9. The system of claim 8, wherein the at least one operating parameter is selected from the group consisting of temperature, impedance, power, current, voltage, mode of operation, and duration of application of electromagnetic energy.

10. The system of claim 8, further comprising a user interface including a screen associated with the handle assembly, the screen communicatively-coupled to the controller.

11. The system of claim 10, wherein the user interface is adapted to enable at least one electrical signal indicative of user input to be transmitted to the controller.

12. The system of claim 1, wherein the microwave-signal-amplifying module includes a first connector portion including a first electrical connector suitable for electrically-coupling the microwave-signal-amplifying module to the probe.

13. The system of claim 12, wherein the microwave-signal-amplifying module includes a second connector portion including a second electrical connector suitable for receiving a high-frequency signal generated by the microwave signal generator, wherein the microwave-signal-amplifying module is adapted to provide an electrical connection between the second electrical connector and the microwave amplifier unit.

* * * * *